(12) United States Patent
Jung et al.

(10) Patent No.: US 10,737,081 B2
(45) Date of Patent: Aug. 11, 2020

(54) PAINLESS AND PATCHLESS SHOOTING MICROSTRUCTURE

(71) Applicant: JUVIC INC., Seoul (KR)

(72) Inventors: Hyung Il Jung, Seoul (KR); Shayan Fakhraeli Lahiji, Seoul (KR)

(73) Assignee: JUVIC INC., Seoul (KR)

( * ) Notice: Subject to any disclaimer, the term of this patent is extended or adjusted under 35 U.S.C. 154(b) by 346 days.

(21) Appl. No.: 15/028,007

(22) PCT Filed: Jun. 17, 2014

(86) PCT No.: PCT/KR2014/005310
§ 371 (c)(1),
(2) Date: Apr. 7, 2016

(87) PCT Pub. No.: WO2014/204176
PCT Pub. Date: Dec. 24, 2014

(65) Prior Publication Data
US 2016/0361527 A1 Dec. 15, 2016

(30) Foreign Application Priority Data
Jun. 17, 2013 (KR) .................. 10-2013-0069102

(51) Int. Cl.
*A61M 37/00* (2006.01)

(52) U.S. Cl.
CPC . *A61M 37/0015* (2013.01); *A61M 2037/0023* (2013.01); *A61M 2037/0046* (2013.01); *A61M 2037/0061* (2013.01)

(58) Field of Classification Search
CPC ........ A61M 37/0015; A61M 2037/003; A61M 2037/0023; A61M 2037/0046;
(Continued)

(56) References Cited

U.S. PATENT DOCUMENTS

| | | | |
|---|---|---|---|
| 2004/0106904 A1* | 6/2004 | Gonnelli | A61B 17/205 604/173 |
| 2005/0055014 A1* | 3/2005 | Coppeta | A61K 9/0009 604/890.1 |

(Continued)

FOREIGN PATENT DOCUMENTS

| KR | 10-0793615 B1 | 1/2008 |
|---|---|---|
| KR | 10-2008-0051342 A | 6/2008 |

(Continued)

OTHER PUBLICATIONS

Sullivan et al., "Minimally Invasive Protein Delivery with Rapidly Dissolving Polymer Microneedles", Adv Mater., 2008, vol. 20, pp. 933-938.

(Continued)

*Primary Examiner* — Kevin C Sirmons
*Assistant Examiner* — Tezita Z Watts
(74) *Attorney, Agent, or Firm* — Knobbe Martens Olson & Bear LLP

(57) ABSTRACT

The present invention relates to a painless and patchless shooting microstructure, and a microstructure shooting device. According to the present invention, it is possible to inject a microstructure into the skin within the time of less than one second, and the inconvenience of waiting for the decomposition of a microstructure and removing a patch are completely overcome. A patch-type conventional technology has a problem wherein it is difficult to be applied to a region having hair, but the present invention completely overcomes this problem. According to the present invention, it is possible to precisely control the permeation depth of a microstructure into the skin by controlling discharge power.

11 Claims, 34 Drawing Sheets

(58) Field of Classification Search
CPC .. A61M 2037/0061; A61M 2037/0053; A61M 5/1428
See application file for complete search history.

(56) References Cited

U.S. PATENT DOCUMENTS

| | | | |
|---|---|---|---|
| 2005/0251088 A1* | 11/2005 | Kwon | A61K 9/0021 604/60 |
| 2010/0298808 A1* | 11/2010 | O'Dea | A61K 9/0021 604/506 |
| 2013/0072902 A1 | 3/2013 | Takada et al. | |
| 2013/0280755 A1* | 10/2013 | Hubert | A61K 9/0019 435/32 |
| 2014/0180201 A1* | 6/2014 | Ding | B29C 43/021 604/46 |

FOREIGN PATENT DOCUMENTS

| | | |
|---|---|---|
| KR | 10-2010-0064669 A | 6/2010 |
| KR | 10-2013-0012838 A | 2/2013 |
| KR | 10-2013-0058703 A | 6/2013 |
| KR | 10-2014-0105397 A | 9/2014 |
| KR | 10-2014-0131879 A | 11/2014 |
| WO | 2009/069112 A1 | 6/2009 |
| WO | 2012/071514 A1 | 5/2012 |

OTHER PUBLICATIONS

Prausnitz et al., "Current status and future potential of transdermal drug delivery", Nature Reviews Drug Discovery, 2004, vol. 3, pp. 115-124.

Prausnitz et al., "Transdermal drug delivery", Nature Biotechnology, Nov. 2008, vol. 26, No. 11, pp. 1261-1268.

Park et al., "Biodegradable polymer microneedles: Fabrication, mechanics and transdermal drug delivery", Journal of Controlled Release, 2005, vol. 104, pp. 51-66.

Trim et al., "A review of sharps injuries and preventative strategies", Journal of Hospital Infection, 2003, vol. 53, pp. 237-242.

Nir et al., "Fear of injections in young adults: prevalence and associations", Am. J. Trop. Med. Hyg., 2003, vol. 68, No. 3, pp. 341-344.

Simonsen et al., "Unsafe injections in the developing world and transmission of bloodborne pathogens: a review", Bulletin of the World Health Organization, 1999, vol. 77, No. 10, pp. 789-800.

Prausnitz, "Microneedles for transdermal drug delivery", Advanced Drug Delivery Reviews, 2004, vol. 56, pp. 581-587.

Tuan-Mahmood et al., "Microneedles for intradermal and transdermal drug delivery", European Journal of Pharmaceutical Sciences, 2013, vol. 50, pp. 623-637.

Lee et al., "Drawing lithography for microneedles: A review of fundamentals and biomedical applications", Biomaterials, 2012, vol. 33, pp. 7309-7326.

McAllister et al., "Microfabricated needles for transdermal delivery of macromolecules and nanoparticles: Fabncation methods and transport studies", PNAS, Nov. 25, 2003, vol. 100, No. 24, pp. 13755-13760.

Kaushik et al., "Lack of Pain Associated with Microfabricated Microneedles", Anesth Analg., 2001, vol. 92, pp. 302-504.

Mikszta et al., "Improved genetic immunization via micromechanical disruption of skin-barrier function and targeted epidermal delivery", Nature Medicine, vol. 8, No. 4, Apr. 2002, pp. 415-419.

Liu et al., "The development and characteristics of novel microneedle arrays fabricated from hyaluronic acid, and their application in the transdermal delivery of insulin", Journal of Controlled Release, 2012, vol. 161, pp. 933-941.

Lee et al., "Drawing Lithography: Three-Dimensional Fabrication of an Ultrahigh-Aspect-Ratio Microneedle", Adv. Mater, 2010, vol. 22, pp. 483-486.

Lee et al., "Dissolving Microneedle Patch for Transdermal Delivery of Human Growth Hormone", Small, 2011, vol. 7, No. 4, pp. 531-539.

Lee et al., "Dissolving microneedles for transdermal drug administration prepared by stepwise controlled drawing of maltose", Biomaterials, 2011, vol. 32, pp. 3134-3140.

Lee et al., "Dissolving microneedles for transdermal drug delivery", Biomaterials, 2008, vol. 29, pp. 2113-2134.

Chu et al., "Separable arrowhead microneedles", Journal of Controlled Release, 2011, vol. 149, pp. 242-249.

Chen et al., "Improving the reach of vaccines to low-resource regions, with a needle-free vaccine delivery device and long-term thermostabilization", Journal of Controlled Release, 2011, vol. 152, pp. 349-355.

Van Damme et al., "Safety and efficacy of a novel microneedle device for dose sparing intradermal influenza iaccination in healthy adults", Vaccine, 2009, vol. 27, pp. 454-459.

Van Der Maaden et al., "Microneedle technologies for (trans)dermal drug and vaccine delivery", Journal of Controlled Release, 2012, vol. 161, pp. 645-655.

Chen et al., "Fully embeddable chitosan microneedles as a sustained release depot for intradermal vaccination", Biomaterials, 2013, vol. 34, pp. 3077-3086.

Sullivan et al., "Dissolving polymer microneedle patches for influenza vaccination", Nature Medicine, Aug. 2010, vol. 16, No. 8, pp. 915-921.

Trookman et al., "Irritation and allergy patch test analysis of topical treatments commonly used in wound care: Evaluation on normal and compromised skin", J Am Acad Dermatol, 2011, vol. 64, No. 3, pp. 16-22.

Kim et al., "Droplet-born air blowing: Novel dissolving microneedle fabrication", Journal of Controlled Release, 2013, vol. 170, pp. 430-436.

Moga et al., "Rapidly-Dissolvable Microneedle Patches Via a Highly Scalable and Reproducible Soft Lithography Approach", Adv. Mater., 2013, vol. 25, pp. 5060-5066.

Taberner et al., "Needle-free jet injection using real-time controlled linear Lorentz-force actuators", Medical Engineering & Physics, 2012, vol. 34, pp. 1228-1235.

Engwerda et al., "Needle-Free Jet Injection of Rapid-Acting Insulin Improves Early Postprandial Glucose Control in Patients With Diabetes", Diabetes Care, Nov. 2013, vol. 36, pp. 3436-3441.

Davis et al., "Insertion of microneedles into skin: measurement and prediction of insertion force and needle fracture force", Journal of Biomechanics, 2004, vol. 37, pp. 1155-1163.

Stachowiak et al., "Dynamic control of needle-free jet injection", Journal of Controlled Release, 2009, vol. 135, pp. 104-112.

Donnelly et al., "Optical coherence tomography is a valuable tool in the study of the effects of microneedle geometry on skin penetration characteristics and in-skin dissolution", Journal of Controlled Release, 2010, vol. 147, pp. 333-341.

Pond et al., "First-Pass Elimination Basic Concepts and Clinical Consequences", Clinical Pharmacokinetics, 1984, vol. 9, pp. 1-25.

International Search Report dated Sep. 1, 2014 of PCT/KR2014/005310 which is the parent application and its English translation—6 pages.

Office Action of corresponding Chinese Patent Application No. 201480045689.8—12 pages (dated Apr. 3, 2018).

\* cited by examiner

PAINLESS AND PATCHLESS SHOOTING MICROSTRUCTURE

TECHNICAL FIELD

This application claims priority to and the benefit of Korean Patent Application No. 2013-0069102, filed on Jun. 17, 2013 in the Korean Intellectual Property Office (KIPO), the disclosure of which is incorporated herein by reference in its entirety.

The present invention relates to a painless and patchless shooting microstructure.

BACKGROUND TECHNOLOGY

A large number of drugs and therapeutic agents have been developed to treat diseases, but problems regarding the passage of drugs through biological barriers (for example, skin, oral mucosae and blood-brain barriers) and the efficiency of drug delivery remain to be solved for in vivo delivery of the drugs.

In general, drugs are orally administered as a tablet formulation or a capsule formulation, but a large number of drugs are not effectively delivered only by such administration method because the drugs are digested in or absorbed into the gastrointestinal tract or are destroyed by mechanisms in the liver, etc. In addition, some drugs cannot be effectively diffused through mucous membranes in the intestines. Also, the patient's compliance also has become a challenge (for example, in the case of critical patients who need to take medicine at certain intervals or cannot take medicine, etc.).

Another common technology for delivering drugs is to use a conventional injection needle. This technology is more effective than oral administration, but may cause pain in an injected area, local damage to skin, bleeding, and infections in the injected area.

To solve the above problems, various microstructures including microneedles have been developed. The microneedles currently developed have been generally used to deliver drugs to human bodies, collect blood, and detect analytes from the human bodies. The microneedles are characterized by piercing the skin in a minimally invasive manner. For painless piercing of the skin, it is important to determine the diameter of a top of the microneedle for the needle's minimum sharpness. Also, since the microneedle needs to pierce the 10 to 20-μm-thick stratum corneum, which is the most potent barrier of the skin, the microneedle needs to have a sufficient physical hardness. Further, a suitable length of the microneedle to deliver drugs to capillary vessels should be considered to enhance the efficiency of drug delivery.

Meanwhile, a microstructure is often fabricated in the form of a patch including a number of microneedles so as to inject the microneedles into the skin. However, the microneedles have a drawback in that, when they are applied to the skin in the form of a patch, a patient must wait until the microneedles are fully dissolved (for approximately 2 hours) before removing the patch. Also, the microneedles in the form of a patch have a limit in application to a hairy region. Further, some people frequently have an allergic reaction to glutinous substances present in the patch.

Dissolving microneedles (DMNs) of the present invention are microneedles obtained by polymer polymerization, and a drug is encapsulated in a matrix of each of the DMNs. Insertion of the DMNs into the skin catalyzes the decomposition of a polymeric compound, and thus the drug is systemically or locally delivered. Unlike a subcutaneous injection, the DMNs are biocompatible and do not produce biologically hazardous materials (3, 20). Also, the DMNs are more dose-efficient than immunization by subcutaneous injection (21-23). In recent years, various patches are being widely used to apply the DMNs, but the drug delivery efficiency is low due to a number of parameters regarding skin elasticity, etc., and the DMNs are not completely inserted into the skin (17, 24, and 25). Further, the compound used in the patch has problems in that it may cause various inflammations or allergic reactions in the skin, and lasting adhesion is difficult when it is applied to a joint area or hairy skin, and patients should wait for a long period of time until the drug is completely dissolved (26).

To solve the problems of the prior art regarding the recent DMN-mediated drug delivery, various methods have been designed (20, 24, 27, and 28). However, these methods have focused on improving the common delivery efficiency of DMNs, but there is no mention of a basic solution to problems regarding the incomplete insertion of the DMN patch.

Therefore, there has been a constant demand for novel microstructures capable of solving the above problems of the prior art.

Throughout this specification, a number of research papers and patent documents are cited and provided in parentheses. The disclosures of the cited research papers and patent documents are incorporated herein by reference in their entirety to more fully describe the state of the art to which the present invention pertains and the contents of the present invention.

DISCLOSURE

Technical Problem

The present inventors have tried to conduct intensive research to develop a method of injecting a microstructure into a subject's skin without any pain and need for a patch. As a result, the present inventors have established a shooting microstructure system for the first time, and found that a microstructure can be injected into the subject's skin for highly improved convenience without any pain and requirement of a patch. Therefore, the present invention has been completed based on these facts.

Accordingly, an aspect of the present invention is to provide a shooting microstructure.

Another aspect of the present invention is to provide a microstructure shooting device.

Other objects and advantages of the present invention are more clearly understood by the following detailed description, appended claims and accompanying drawings.

Technical Solution

The present invention provides a shooting microstructure and a microstructure shooting device.

The present inventors have tried to conduct intensive research to develop a method of injecting a microstructure into a subject's skin without any pain and need for a patch, established a shooting microstructure system for the first time, and found that a microstructure can be injected into the subject's skin for highly improved convenience without any pain and need for a patch using such a technique.

Shooting Microstructure

The shooting microstructures of the present invention may be mainly divided into two categories:

1. Shooting Microstructure Including Microstructures Fabricated on a Main Layer According to one aspect of the present invention, the present invention provides a shooting microstructure including:

(a) a main layer configured to support microstructures and having holes formed therein; and (b) microstructures fabricated on the main layer to be supported by immediately adjacent planes of the holes of the main layer.

Basically, a shooting microstructure 10 according to one aspect of the present invention includes a main layer 101 and microstructures 102 formed on a surface 101b of the main layer (see FIG. 1A). Hereinafter, the shooting microstructure according to one aspect is referred to as a "shooting microstructure I."

As a support layer, the main layer 101 provides support planes on which the microstructures 102 may be fabricated. When the microstructures 102 are injected into the skin, holes 101a of the main layer 101 serve to easily separate the microstructures 102 from the main layer 101, and also serve to transmit a pushing pressure to a bottom part of each of the microstructures.

2. Shooting Microstructure Including Microstructures Formed on a Base Layer

According to another aspect of the present invention, the present invention provides a shooting microstructure including:

(a) a main layer configured to support microstructures and having holes formed therein;

(b) a base layer which is arranged on the main layer and on which the microstructures are fabricated; and (c) microstructures fabricated on the base layer.

Basically, a shooting microstructure 20 according to another aspect of the present invention includes a main layer 201, a base layer 204, and microstructures 202 fabricated on a surface 204b of the base layer. Hereinafter, the shooting microstructure according to another aspect is referred to as a "shooting microstructure II."

According to one embodiment of the present invention, the base layer 204 has holes 204a formed therein, and the microstructures are fabricated on the base layer to be supported by immediately adjacent planes of the holes 204a of the base layer. A hole may be formed at a size similar to or smaller than an area on which a microstructure (for example, a microneedle) are fabricated. That is, the area or size of the hole may be properly adjusted according to the microstructures, the base layer, or the main layer. When the material of the microstructures, the base layer, or the main layer is a polymer, the size of the hole should be adjusted according to physicochemical properties of the polymer (for example, viscosity, surface tension, a change in physical properties according to a temperature, etc.). Meanwhile, the base layer 204 may be manufactured in a state in which the base layer 204 has no holes 204a (see FIG. 20). When the base layer 204 has no holes, the base layer may be injected into the skin together with the microstructures as movable pillars are inserted into the skin. In this case, the base layer may be a biocompatible substance, that is, a biodegradable substance or a biodegradable substance including a pharmaceutical composition.

As a support layer, the base layer 204 provides support planes on which the microstructures 202 may be fabricated. When the microstructures 202 are injected into the skin, holes 201a of the main layer 201 and/or the holes 204a of the base layer 204 serve to easily separate the microstructures 202 from the base layer 204. The holes 201a of the main layer 201 and/or the holes 204a of the base layer 204 serve to transmit a pushing pressure to a bottom part of each of the microstructures.

In comparison to the shooting microstructure I, the shooting microstructure II further includes the base layer 204. The base layer 204 may be more strongly coupled to the microstructures than the main layer 101 or 201, and facilitates fabrication of the microstructures.

The shooting microstructure I and the shooting microstructure II will be described in further detail, as follows:

The shooting microstructure of the present invention is a microstructure configured to separate the microstructures from the support layer (a main layer in the case of the shooting microstructure I and the base layer in the case of the shooting microstructure II) so that only the microstructures are easily injected into the skin. For example, when a force is applied to the support layer on which the microstructures are fabricated, the force serves to separate the microstructures from the support layer and also serves to allow the separated microstructures to have kinetic energy so that the separated microstructures can be injected into the skin. The microstructure having this operation principle is referred to as a "shooting microstructure" in this specification. In this case, this shooting microstructure is first presented by the present inventors. In the present invention, a microneedle is used as one example of the microstructure.

In the shooting microstructure I, the microstructures 102 are fabricated on the surface 101b of the main layer 101 to be supported by immediately adjacent planes of the holes 101a of the main layer 101 serving as the support layer.

For example, when a biocompatible polymer having viscosity is spotted on the holes 101a of the main layer, most spots have a lager diameter than the holes. Since the spots are viscous even when the spots have a smaller diameter than the holes, the spots may be attached to immediately adjacent inner planes (inner lateral planes) of the holes. When the spots are extended, the microstructures may be fabricated on the main layer 101 to be supported by immediately adjacent planes (including both immediately adjacent outer planes of the holes and inner lateral planes of the holes) of the holes 101a of the main layer 101.

The extension of the spots may be performed using various methods. For example, the microstructures may be fabricated by bringing a frame having protrusions into contact with spots and then drawing the spots upwards using a method as disclosed in Korean Patent No. 0793615 previously filed by the present inventors. Also, the microstructures may be fabricated by applying a negative pressure to the spots as disclosed in Korean Unexamined Patent Application Publication No. 2013-0019247 previously filed by the present inventors. In addition, the microstructures may be fabricated by applying a centrifugal force to a viscous composition to induce extension of the viscous composition, as disclosed in Korean Unexamined Patent Application Publication No. 2013-0050462 (claiming priority to Korean Patent Application Publication No. 2014-0053423) previously filed by the present inventors.

The shooting microstructure II may be mainly manufactured by two methods:

In the first method, when the base layer 204 has no holes, a viscous biocompatible polymer is coated or spotted on a surface of the base layer 204. Thereafter, the viscous biocompatible polymer is extended to fabricate the microstructures using the method disclosed in Korean Patent No. 0793615 previously filed by the present inventors and the method disclosed in Korean Unexamined Patent Application Publication No. 2013-0019247.

In the second method, when the base layer 204 has the holes 204a, the microstructures 202 are fabricated on the surface 204b of the base layer 204 to be supported by immediately adjacent planes of the holes 204a of the base layer 204 serving as the support layer. For example, when the viscous biocompatible polymer is spotted on the holes 204a of the base layer, most of the spots have a larger diameter than the holes. Since the spots are viscous even when the spots have a smaller diameter than the holes, the spots may be attached to immediately adjacent inner planes of the holes. When the spots are extended, the microstructure may be fabricated on the base layer 204 to be supported by immediately adjacent plane of the holes 204a of the base layer 204. The extension of the spots may be performed by various methods, for example, performed by the method disclosed in Korean Patent No. 0793615 previously filed by the present inventors, and the method disclosed in Korean Unexamined Patent Application Publication No. 2013-0019247.

According to one embodiment of the present invention, the shooting microstructure further includes a protection layer 103 or 203 having holes 103a or 203a formed therein. Here, the holes 103a or 203a of the protection layer has a larger diameter than bottom parts of the microstructures 102 or 202, and surround peripheries of the microstructures 102 or 202 to protect the microstructures 102 or 202. Also, when microneedles are separated to be shot, the protection layer 103 or 203 serves to shoot only the microneedles without shooting regions of the base layer or the main layer coupled to the bottom parts of the microneedles.

According to one embodiment of the present invention, the microstructures 102 or 202 are separated from the main layer 101 or 201 or the base layer 204 to be shot due to a pushing pressure transmitted to the bottom parts of the microstructures 102 or 202 through the holes 101a or 201a of the main layer.

In this specification, the term "shooting" used with reference to the microstructures means that the microstructures are separated from the main layer 101 or 201 or the base layer 204 to move forward.

When the pushing pressure is applied to the bottom parts of the microstructures 102 or 202 through the holes 101a or 201a of the main layer, the microstructures 102 or 202 have a weaker coupling strength than the microstructures coupled to a typical substrate. As a result, the microstructures 102 or 202 are relatively easily separated from the main layer 101 or 201 or the base layer 204 to be shot.

The pushing pressure may include any pushing pressures as long as they act to separate the microstructures 102 or 202 from the main layer 101 or 201 or the base layer 204 to move forward. The pushing pressure may be generated and applied by various methods. For example, a pushing pressure may be generated and applied using the air or an article (for example, a bar).

A specific means for applying a pushing pressure to the shooting microstructure is shown in FIG. 2. A shooting device 30 of FIG. 2 includes a top part 302 having a plurality of holes 302a formed therein and configured to accommodate a shooting microstructure; and a body part 301 configured to transmit a pushing pressure to the plurality of holes 302a and including a pushing pressure transmission channel openly connected to the plurality of holes. When the pushing pressure is transmitted to bottom parts of the microstructures through the plurality of holes 302a, the microstructures are separated from the main layer 101 or 201 or the base layer 204 to be shot. The shooting device will be described in detail, as follows.

A substance used in the present invention to fabricate the microstructures is a viscous composition. In this specification, the term "viscous composition" refers to a composition having an ability to change its shape to fabricate microstructures.

The viscosity of such a viscous composition may vary to a wide extent, depending on the type concentration or temperature of the substance included in the composition, or addition of a viscosity modifying agent, and may be properly adjusted according to the objects of the present invention. The viscosity of the viscous composition may be adjusted by an innate viscosity of a viscous substance, and may also be adjusted using an additional viscosity modifying agent included in the viscous composition.

For example, a viscosity modifying agent typically used in the art, for example, a viscosity modifying agent such as hyaluronic acid and salts thereof, polyvinyl pyrrolidone, a cellulose polymer, dextran, gelatine, glycerine, polyethylene glycol, polysorbate, propylene glycol, povidone, carbomer, gum ghatti, guar gum, glucomannan, glucosamine, a dammar resin, rennet casein, locust bean gum, microfibrillated cellulose, *psyllium* seed gum, xanthan gum, arabinogalactan, Arabia gum, alginic acid, gelatine, gellan gum, carrageenan, karaya gum, curdlan, chitosan, chitin, tara gum, tamarind gum, tragacanth gum, furcelleran, pectin, or pullulan, may be added to a composition including a main component of the microstructure, for example, a biocompatible substance to properly adjust the viscosity of the viscous composition according to the present invention. Preferably, the viscous composition used in the present invention has a viscosity of 200,000 cSt or less.

According to one embodiment of the present invention, the viscous composition used in the present invention includes a biocompatible or biodegradable substance. In this specification, the term "biocompatible substance" refers to a substance that is not substantially toxic to human bodies, is chemically inert and has no immunogenicity. In this specification, the term "biodegradable substance" refers to a substance that may be degraded by a body fluid or microorganisms in the human body.

According to one embodiment of the present invention, the viscous composition used in the present invention includes hyaluronic acid and salts thereof, polyvinyl pyrrolidone, a cellulose polymer (for example, hydroxypropyl methylcellulose, hydroxyalkyl cellulose, hydroxyethyl cellulose, hydroxypropyl cellulose, ethyl hydroxyethyl cellulose, alkyl cellulose, and carboxymethyl cellulose), dextran, gelatine, glycerine, polyethylene glycol, polysorbate, propylene glycol, povidone, carbomer, gum ghatti, guar gum, glucomannan, glucosamine, dammer resin, rennet casein, locust bean gum, microfibrillated cellulose, *psyllium* seed gum, xanthan gum, arabinogalactan, Arabia gum, alginic acid, gelatine, gellan gum, carrageenan, karaya gum, curdlan, chitosan, chitin, tara gum, tamarind gum, tragacanth gum, furcelleran, pectin, or pullulan.

Optionally, the viscous composition may include a biocompatible and/or biodegradable substance as a main component.

The biocompatible and/or biodegradable substance that may be used in the present invention, for example, includes a polyester, a polyhydroxyalkanoate (PHA), poly($\alpha$-hydroxy acid), poly($\beta$-hydroxy acid), poly(3-hydroxybutyrate-co-valerate) (PHBV), poly(3-hydroxypropionate) (PHP), poly(3-hydroxyhexanoate) (PHH), poly(4-hydroxy acid), poly(4-hydroxybutyrate), poly(4-hydroxyvalerate), poly(4-hydroxyhexanoate), poly(esteramide), polycaprolactone, polylactide, polyglycolide, poly(lactide-co-glycolide)

(PLGA), polydioxanone, polyorthoester, polyetherester, polyanhydride, poly(glycolic acid-co-trimethylene carbonate), polyphosphoester, polyphosphoester urethane, poly(amino acid), polycyanoacrylate, poly(trimethylene carbonate), poly(iminocarbonate), poly(tyrosine carbonate), a polycarbonate, poly(tyrosine arylate), polyalkylene oxalate, a polyphosphazene, PHA-PEG, an ethylene vinyl alcohol copolymer (EVOH), a polyurethane, silicone, a polyester, a polyolefin, a copolymer of polyisobutylene and ethylene-alpha olefin, a styrene-isobutylene-styrene triblock copolymer, an acrylic polymer and copolymer, a vinyl halide polymer and copolymer, polyvinyl chloride, polyvinyl ether, polyvinyl methyl ether, a polyvinylidene halide, polyvinylidene fluoride, polyvinylidene chloride, polyfluoroalkene, polyperfluoroalkene, polyacrylonitrile, polyvinyl ketone, polyvinyl aromatics, polystyrene, polyvinyl ester, polyvinyl acetate, an ethylene-methyl methacrylate copolymer, an acrylonitrile-styrene copolymer, a copolymer of ABS resin and ethylene-vinyl acetate, a polyamide, an alkyd resin, polyoxymethylene, a polyimide, a polyether, a polyacrylate, a polymethacrylate, polyacrylic acid-co-maleic acid, chitosan, dextran, cellulose, heparin, hyaluronic acid, alginate, inulin, starch, or glycogen, preferably a polyester, a polyhydroxyalkanoate (PHA), poly($\alpha$-hydroxy acid), poly($\beta$-hydroxy acid), poly(3-hydroxybutyrate-co-valerate) (PHBV), poly(3-hydroxypropionate) (PHP), poly(3-hydroxyhexanoate) (PHH), poly(4-hydroxy acid), poly(4-hydroxybutyrate), poly(4-hydroxyvalerate), poly(4-hydroxyhexanoate), poly(esteramide), polycaprolactone, polylactide, polyglycolide, poly(lactide-co-glycolide) (PLGA), polydioxanone, polyorthoester, polyetherester, polyanhydride, poly(glycolic acid-co-trimethylene carbonate), polyphosphoester, polyphosphoester urethane, poly(amino acid), polycyanoacrylate, poly(trimethylene carbonate), poly(iminocarbonate), poly(tyrosine carbonate), a polycarbonate, poly(tyrosine arylate), polyalkylene oxalate, a polyphosphazene, PHA-PEG, chitosan, dextran, cellulose, heparin, hyaluronic acid, alginate, inulin, starch, or glycogen.

According to one embodiment of the present invention, the viscous composition used in the present invention is dissolved in a suitable solvent to exhibit viscosity. Meanwhile, among the substances exhibiting viscosity, some substances exhibit viscosity only when the substances are melted by heat. The solvent used to dissolve the viscous substance to prepare the viscous composition is not particularly limited. For example, water, an anhydrous or hydrous lower alcohol having 1 to 4 carbon atoms, acetone, ethyl acetate, chloroform, 1,3-buthylene glycol, hexane, diethylether or butyl acetate may be used as the solvent.

According to one embodiment of the present invention, each of the microstructures 102 or 202 further includes a drug. One use of the microstructure of the present invention is as a microneedle, which is used for the purpose of percutaneous administration. Therefore, the drug is mixed with the biocompatible substance during the preparation of the viscous composition.

The drug that may be used in the present invention is not particularly limited. For example, the drug includes a chemical, a protein medicine, a peptide medicine, nucleic acid molecules for gene therapy, nanoparticles, an active ingredient for functional cosmetics, and a cosmetic ingredient.

The drug that may be used in the present invention, for example, includes an anti-inflammatory agent, an analgesic agent, an antiarthritic agent, an antispasmodic agent, an antidepressant, an antipsychotic drug, a tranquilizer, an antianxiety drug, a narcotic antagonist, an anti-Parkinson's disease drug, a cholinergic agonist, an anticancer drug, an anti-angiogenesis inhibitor, an immunosuppressant, an antiviral agent, an antibiotic, an appetite suppressant, an analgesic agent, an anticholinergic drug, an antihistaminic agent, an antimigraine agent, a hormone drug, a coronary, cerebrovascular or peripheral vasodilator, a contraceptive pill, an antithrombotic drug, a diuretic drug, an antihypertensive drug, a cardioprotective agent, a cosmetic ingredient (for example, an anti-wrinkle agent, an anti-skin-aging agent, and a skin whitening agent), etc., but the present invention is not limited thereto.

According to one embodiment of the present invention, a method of fabricating the microstructures 102 or 202 according to the present invention is performed at room temperature or a low temperature (for example, 5 to 20° C.) less than the room temperature under non-heating treatment conditions. Therefore, although the drug used in the present invention is a drug vulnerable to heat, such as a protein medicine, a peptide medicine, nucleic acid molecules for gene therapy, etc., it is possible to fabricate the microstructures including the drug according to the present invention.

The protein/peptide medicine encapsulated in each of the microstructures 102 or 202 of the present invention is not particularly limited, and includes a hormone, a hormone analogue, an enzyme, an enzyme inhibitor, a signaling protein or fragments thereof, an antibody or fragments thereof, a single-chain antibody, a binding protein or binding domains thereof, an antigen, an adhesion protein, a structural protein, a regulatory protein, a toxoprotein, a cytokine, a transcriptional regulatory factor, a blood coagulation factor, and a vaccine, but the present invention is not limited thereto. More specifically, the protein/peptide medicine includes insulin, an insulin-like growth factor 1 (IGF-1), a growth hormone, erythropoietin, a granulocyte-colony stimulating factor (G-CSF), a granulocyte/macrophage-colony stimulating factor (GM-CSF), interferon-alpha, interferon-beta, interferon-gamma, interleukin-1 alpha and beta, interleukin-3, interleukin-4, interleukin-6, interleukin-2, an epidermal growth factor (EGF), calcitonin, an adrenocorticotropic hormone (ACTH), a tumor necrosis factor (TNF), atobisban, buserelin, cetrorelix, deslorelin, desmopressin, dynorphin A (1-13), elcatonin, eleidosin, eptifibatide, growth hormone releasing hormone-II gonadorelin, goserelin, histrelin, leuprorelin, lypressin, octreotide, oxytocin, pitressin, secretin, sincalide, terlipressin, thymopentin, thymosine $\alpha 1$, triptorelin, bivalirudin, carbetocin, cyclosporine, exedine, lanreotide, a luteinizing hormone-releasing hormone (LHRH), nafarelin, a parathyroid hormone, pramlintide, T-20 (enfuvirtide), thymalfasin, and ziconotide.

According to one embodiment of the present invention, each of the microstructures 102 or 202 further includes an energy storage unit. In this case, the microstructures 102 or 202 may be used to send or transmit a type of energy such as heat energy, light energy, electric energy, etc. For example, for photodynamic therapy, the microstructures 102 or 202 may be used to guide light to a certain region in a human body so that the light acts directly on tissues or acts on a mediator such as light-sensitive molecules.

In the present invention, the microstructures may be in various shapes, for example, may be in the form of a microneedle, a microblade, a microknife, a microfiber, a microspike, a microprobe, a microbarb, a microarray, or a microelectrode.

In the present invention, the microstructures may have various dimensions. For example, the microstructures in the present invention has a tip diameter of 1 to 500 µm, 2 to 300

μm, or 5 to 100 μm, and an effective length of 100 to 10,000 μm, 200 to 10,000 μm, 300 to 8,000 μm, or 500 to 2,000 μm. The term "tip" of the microstructure used in this specification refers to one end portion of the microstructure having the minimum diameter. The term "effective length" used in this specification refers to a vertical length from a tip of the microstructure to a surface of a support. The term "bottom part" used in this specification refers to one end portion of the microstructure having the maximum diameter. For example, the microstructures in the present invention have a bottom diameter 50 to 1,000 μm and an effective length of 100 to 10,000 μm.

In the shooting microstructure of the present invention, the main layer 101 or 201 may be manufactured using various substances. For example, the main layer 101 or 201 may be manufactured using a substance such as a polymer, an organic chemical substance, a metal, a ceramic, a semiconductor material, etc. According to one embodiment, the main layer 101 or 201 is manufactured using a metal. When the main layer is manufactured using a metal, the main layer may be coupled to the shooting microstructure due to magnetism. The thickness of the main layer 101 or 201 is not particularly limited, and is, for example, in a range of 0.001 to 10 mm, 0.01 to 1 mm, 0.08 to 0.5 mm, 0.08 to 0.2 mm, or 0.09 to 0.15 mm.

In the shooting microstructure of the present invention, the base layer 204 may be manufactured using various substances. According to one embodiment of the present invention, the base layer 204 is manufactured using a viscous composition. The viscous composition that may be used for the base layer 204 will be described with reference to the viscous composition and biocompatible substance used to fabricate the microstructures. The base layer may be manufactured using a substance which is the same as or different from those of the microstructures. The thickness of the base layer 204 is not particularly limited, and is, for example, in a range of 0.1 to 1,000 μm, 1 to 100 μm, 1 to 50 μm, or 1 to 10 μm.

In the shooting microstructure of the present invention, the protection layer 103 or 203 may be manufactured using various substances. For example, the protection layer 103 or 203 may be manufactured using a substance such as a polymer, an organic chemical substance, a metal, a ceramic, a semiconductor material, etc. According to one embodiment, the protection layer 101 or 201 is manufactured using a metal. When the protection layer is manufactured using a metal, the protection layer may be coupled to the shooting microstructure due to the magnetism. The thickness of the protection layer 103 or 203 is not particularly limited since the thickness of the protection layer is dependent on the length of a microneedle. For example, when the microneedle has a length of 100 to 1,000 μm, the thickness of the protection layer is in a range of 100 to 1,000 μm.

In the shooting microstructure of the present invention, the size of holes formed in the main layer, the base layer and the protection layer is not particularly limited. For example, the diameter of the holes is in a range of 10 to 5,000 μm, 100 to 4,000 μm, 500 to 4,000 μm, 800 to 4,000 μm, 800 to 3,000 μm, 900 to 2,000 μm, or 900 to 1500 μm. The holes may be introduced by various methods. For example, the holes may be introduced using a laser cutting device.

According to one embodiment of the present invention, in the shooting microstructure I, the main layer has the plurality of holes 101a. According to one embodiment of the present invention, in the shooting microstructure II, the main layer and the base layer have the plurality of holes 201a and holes 204a, respectively.

Such a plurality of holes are properly formed when the shooting microstructure includes a plurality of microstructures.

According to one embodiment of the present invention, the plurality of holes of the main layer and the base layer are formed at corresponding positions. According to one embodiment, the plurality of holes of the main layer, the base layer and the protection layer are formed at corresponding positions. According to one embodiment, the plurality of holes of the main layer, the base layer, the protection layer and the shooting device are formed at corresponding positions. In this case, a pushing pressure is applied to the bottom parts of the microstructures through the plurality of holes formed at such corresponding positions to shoot the microstructures.

According to one embodiment of the present invention, the plurality of holes 101a or 201a of the main layer have the same diameter as those of the bottom parts of the microstructures 102 or 202 (see FIG. 4A).

According to one embodiment of the present invention, the plurality of holes 101a or 201a of the main layer have a smaller diameter than those of the bottom parts of the microstructures 102 or 202 (see FIG. 4B). In this case, the shooting microstructure of the present invention is favorable for directly fabricating the microstructures on the main layer.

According to one embodiment of the present invention, the plurality of holes 101a or 201a of the main layer have a larger diameter than those of the bottom parts of the microstructures 102 or 202 (see FIG. 4C). In this case, for fabrication of the microstructures, it is desirable to fill the holes 101a or 201a of the main layer, fabricate the microstructures and then remove the filling.

According to one embodiment of the present invention, the plurality of holes 204a of the base layer have a larger diameter than the holes 201a of the main layer. According to another embodiment, the plurality of holes 204a of the base layer have the same diameter as the plurality of holes 201a of the main layer. According to one embodiment, the plurality of holes 204a of the base layer have a smaller diameter than the plurality of holes 201a of the main layer.

According to one embodiment of the present invention, regions of the base layer on which the microstructures are fabricated have a weaker strength than the other regions of the base layer (see FIG. 5). As shown in FIG. 5, the microstructures may be more effectively shot due to such weak and strong pattern coating.

Meanwhile, the shooting microstructure of the present invention may further include movable pillars arranged on immediately adjacent planes of the main layer. The movable pillars protrude out of the shooting microstructure through the holes formed in the main layer and the protection layer due to the pushing pressure (see FIG. 22). In this case, each of the movable pillars does not require an additional support, and is manufactured in a state in which the movable pillars are slightly inserted into the holes of the main layer at the beginning. As a result, the movable pillars may protrude through the holes without an additional aligner or a body part.

Microstructure Shooting Device I

According to another aspect of the present invention, the present invention provides a microstructure shooting device includes (a) a top part configured to accommodate the shooting microstructure of the present invention; and (b) a body part configured to transmit a pushing pressure (i.e., a pushing force) to holes formed in the shooting microstructure and capable of being openly connected to the holes.

The microstructure shooting device I of the present invention uses the above-described shooting microstructure of the present invention, and thus description of the common contents between the microstructure shooting device I and the shooting microstructure will be omitted to avoid excessive complexity of the description in this specification.

The shooting device of the present invention is designed to be suitable for shooting the above-described shooting microstructure of the present invention, and thus is used in the same meaning as a microlancer in this specification (see FIGS. 2, 3 and 10).

The microstructure shooting device of the present invention is a system capable of directly delivering a patch-less or needle-less drug into the skin, and may apply a force through finely movable pillars to infiltrate a target drug into the skin at a high speed.

In recent years, a microneedle array has often been combined with a patch and used. However, such a patch is also affected by various factors such as the presence or absence and amount of hair in the skin, the elasticity of the skin, etc., which makes it impossible to completely insert the microneedle array into the skin. Based on these facts, the present inventors have designed a microstructure shooting device (or a microlancer) including self-injectable microneedles, and found that the delivery efficiency of a target drug may approximate 100% using the microstructure shooting device of the present invention.

When the microstructure shooting device of the present invention is used, the microneedles may be accurately inserted to a desired range of depth regardless the type of the skin and the presence or absence of hair. In a Franz diffusion cell test, the drug delivery efficiency is 97±3%, which is significantly different from the control whose drug delivery efficiency is 56±5% (see Example 2). Also, in the present invention, it was confirmed that, when the microlancer of the present invention is applied to diabetogenic mice, the drug delivery is approximately 40% or more effective, compared to when the patch is used.

In this specification, the term "microlancer" refers to a patch-less, self-injectable DMN delivery system. The microlancer of the present invention may be used to inject drug-loaded DMNs into the skin with the minimum invasion without using a patch. Accordingly, such a microlancer of the present invention presents a solution to basic problems which have not been solved by conventional jet injectors.

The dissolving microneedles (DMNs) of the present invention may be manufactured with a certain alignment array (see FIG. 1C).

Hereinafter, the microstructure shooting device I of the present invention will be described in detail:

The holes 302a capable of being openly connected to the holes formed in the shooting microstructure may be formed in the top part 302 of the shooting device 30. Here, the holes 302a serve to transmit a pushing pressure to a bottom part of the microstructures 102 or 202. The holes 302a may be present in a plural number.

According to one embodiment of the present invention, the pushing pressure used in the present invention includes a pressure caused by various forces, for example, a physical pressure or a chemical pressure. For example, the physical pressure includes a pressure caused by the air, a pressure caused by a mechanical force, a pressure caused by elasticity, and a physical force (i.e., a finger force) by human beings, but the present invention is not limited thereto. The chemical pressure includes a pressure caused by changes in temperature, volume, viscosity, surface tension, concentration or chemical structure by chemical reaction and addition of a compound, but the present invention is not limited thereto.

The shooting device 30 includes a pushing pressure transmission channel configured to transmit a pushing pressure to the holes 302a and openly connected to the holes. Although not shown in FIG. 2, the pushing pressure transmission channel is arranged inside the body part 301, and serves as a passage through which a pushing pressure generated from a pushing pressure generation unit (for example, an air pressure generation unit) is transmitted to the plurality of holes.

The shooting device 30 further includes a connection part 303 configured to connect the shooting device to the pushing pressure generation unit. The connection part 303 may be formed outside the shooting device, as shown in FIG. 2, and may also be formed inside the shooting device.

The shooting device 30 further includes the pushing pressure generation unit configured to apply a pushing pressure to the pushing pressure transmission channel. FIG. 10 shows the pushing pressure generation unit inserted into the shooting device, and FIG. 11 shows that connection parts 410 and 411 are formed below pushing pressure generation units 403a, 403b, 403c and 404 and microstructures are connected to a bottom part of the connection part. That is, a pushing pressure may be generated using springs configured to generate a physical force, a button, a switch, etc.

According to one embodiment of the present invention, a pushing pressure is applied to the microstructures using springs 403a, 403b and 403c, a button 404, the connection pipes 410 and 411, and an auxiliary pipe 409. Each of the springs includes one injecting spring 403a and two extracting springs 403b and 403c; the connection pipes 410 and 411 connect the extracting spring 403b to the injecting spring 403a, and a pin hole 410a through which a pin 405 may be inserted is formed in the connection pipe 410; the shooting microstructure is coupled to an end portion of the connection pipe 411; and the injecting spring 403a is arranged inside the auxiliary pipe 409, the extracting spring 403c is arranged outside the auxiliary pipe, and a slope along which the pin 405 is movable is formed in the auxiliary pipe.

The pin 405 is inserted across both the slope 409a formed in the auxiliary pipe 409 and the pin hole 410a formed in the connection pipe 410. Therefore, the injecting spring 403a is present in a slightly contracted state before a pressure is applied to the shooting device.

Once a pressure is applied to the button 404, the injecting spring 403a and the extracting spring 403c are contracted, and the pin 405 gradually moves upwards along the slope 409a of the auxiliary pipe, that is, moves toward the button 404. When a force greater than a predetermined load is applied, the pin escapes from the slope to rapidly move downwards, and a downward pressure is simultaneously applied to the connection pipes 410 and 411 while the injecting spring is returning to an original state. As a result, the microstructures connected to the connection pipes are inserted into the skin. As viewed from the outside of the device, it seems that the pin moves laterally with respect to a groove 402a while a force is being applied, and the pin moves downwards from the groove 402a at the moment at which the pin escapes from the slope. After an injection process is completed, when the pressure applied to the button 404 is removed, the pillars get back into a body part 402 of the device while the two extracting springs 403b and 403c return to original states.

Meanwhile, methods of shooting the shooting microstructure using the pushing pressure generated in the shooting device 30 may be mainly divided into three categories:

According to the first method (see FIGS. 6A and 6B), the pushing pressure generated by the pushing pressure generation unit is transmitted to a bottom part of the microstructures 102 or 202 through the plurality of holes 302*a* formed in the top part 302 of the shooting device 30, and thus the microstructures 102 or 202 are shot. A shooting rate (or kinetic energy) of the microstructures may be adjusted under the control of an air pressure to adjust a depth of permeation of the microstructures 102 or 202 into the skin.

The second method uses the movable pillars (see FIGS. 7A and 7B). When the movable pillars that may be input/output into/from the holes 302*a* move forwards, the pushing pressure is transmitted to the bottom parts of the microstructures 102 or 202, thereby shooting the microstructures 102 or 202. The shooting rate (or kinetic energy) of the microstructures may be adjusted under the control of a moving speed of the pillars to adjust a depth of permeation of the microstructures 102 or 202 into the skin. After the microstructures 102 or 202 are pierced into the skin, the pillars return to original positions.

According to one embodiment of the present invention, the shooting device 30 further includes movable pillars arranged in the pushing pressure transmission channel, and the movable pillars protrude to a higher height than the top part 302 through the holes 302*a* due to the pushing pressure.

The third method is a combination of the first and second methods (see FIGS. 8A and 8B). In this case, hollow movable pillars are used. When the hollow movable pillars that may be input/output into/from the holes 302*a* move forwards, the pushing pressure is transmitted to the bottom parts of the microstructures 102 or 202, thereby shooting the microstructures 102 or 202. Then, when an air pressure is applied through the holes of the pillars, the microstructures 102 or 202 move deeper into the skin. Optionally, the pushing pressure caused by the pillars and the pushing pressure caused by the air through the holes may be applied at the same time so that the microstructures 102 or 202 are pierced into the skin. The moving speed and air pressure of the pillars may be controlled to adjust a depth of permeation of the microstructures 102 or 202 into the skin.

According to one embodiment of the present invention, the movable pillars has a hollow structure including holes, and a pushing pressure is transmitted to the bottom parts of the shooting microstructures 102 or 202 through the holes.

According to one embodiment of the present invention, the device 30 of the present invention may be installed inside the body part, and may further include a spacer configured to adjust a discharge height of the movable pillars.

According to one embodiment of the present invention, the device 30 of the present invention may further include an aligner configured to provide a moving path for the movable pillars.

According to one embodiment of the present invention, the device 30 of the present invention further includes the shooting microstructure 10 or 20 fabricated on the top part 302.

Microstructure Shooting Device II

According to still another aspect of the present invention, the present invention provides a microstructure shooting device capable of being coupled to the shooting microstructure of the present invention and configured to transmit a pushing pressure (i.e., a pushing force) to holes formed in a main layer or a base layer of the shooting microstructure so that microstructures formed on the main layer or the base layer are separated from the main layer or the base layer to be shot due to the pushing pressure. Here, the device includes (a) a hollow body part openly connected to the holes; (b) a pushing pressure generation unit arranged in the hollow body part and configured to apply a pushing pressure to the microstructures; and (c) movable pillars arranged inside the hollow body part and protruding out of the device through the holes due to the pushing pressure.

The microstructure shooting device II of the present invention uses the same operation principle as that of the above-described shooting microstructure and microstructure shooting device I of the present invention, and thus description of the common contents between the microstructure shooting devices I and II will be omitted to avoid excessive complexity of the description in this specification.

According to one embodiment of the present invention, the main layer or the base layer has a plurality of holes in the device of the present invention.

A pushing pressure configured to move the movable pillars through the holes is a physical pressure or a chemical pressure. Examples of the pushing pressure are as described above.

According to one embodiment of the present invention, the device of the present invention may further include a spacer detachable from an inner or outer part of the body part and configured to adjust a discharge height of the movable pillars.

According to one embodiment of the present invention, the device of the present invention may further include an aligner detachable from an inner or outer part of the device and configured to provide a moving path for the movable pillars.

The device of the present invention may have a structure in which the shooting microstructure of the present invention is coupled to the inner or outer part of the device.

Microstructure Shooting Device III

According to still another aspect of the present invention, the present invention provides a microstructure shooting device including:

(a) a shooting microstructure including the following configuration (i) or (ii): (i) a shooting microstructure including (i-1) a main layer configured to support microstructures and having holes formed therein, and (i-2) microstructures fabricated on the main layer to be supported by immediately adjacent planes of holes of the main layer, or (ii) a shooting microstructure including (ii-1) a main layer configured to support microstructures and having holes formed therein, (ii-2) a base layer which is arranged on the main layer and on which the microstructures are fabricated, and (ii-3) microstructures fabricated on the base layer; and (b) a body part capable of being coupled to the shooting microstructure and configured to transmit a pushing pressure (i.e., a pushing force) to holes formed in the main layer or the base layer of the shooting microstructure.

The microstructure shooting device III of the present invention uses the same operation principle as that of the above-described shooting microstructure and microstructure shooting device I of the present invention, and thus description of the common contents between the microstructure shooting devices I and III will be omitted to avoid excessive complexity of the description in this specification.

The body part may be coupled to the shooting microstructure of the present invention, and transmits a pushing pressure (i.e., a pushing force) to the holes formed in the main layer or the base layer of the shooting microstructure. Also, the shooting microstructure may be accommodated in the body part, or the shooting microstructure may be detached from the outside of the body part.

According to one embodiment of the present invention, the holes formed in the main layer or the base layer of the shooting microstructure may be present in a plural number in the device of the present invention.

According to one embodiment of the present invention, the device of the present invention includes a pushing pressure transmission channel openly connected to the holes arranged inside the body part.

According to one embodiment of the present invention, the pushing pressure applied to the device of the present invention is a physical pressure or a chemical pressure. Examples of the pushing pressure are as described above.

According to one embodiment of the present invention, the device of the present invention may further include a pushing pressure generation unit configured to apply a pushing pressure.

The device of the present invention includes movable pillars arranged inside or outside the body part, and the movable pillars protrude out of the body part through the holes due to the pushing pressure.

The device of the present invention may further include a spacer detachable from an inner or outer part of the body part and configured to adjust a discharge height of the movable pillars, and also may further include an aligner detachable from the inner or outer part of the body part and configured to provide a moving path for the movable pillars.

The microstructure shooting device of the present invention may be manufactured for a single use. When the microstructure shooting device is manufactured for a single use, the microstructure shooting device further includes a sealing layer (i.e., a sealer) detachable from the device and configured to protect the shooting microstructure from external environments (see FIGS. 18 to 21). Such a sealing layer may be attached to the inner or outer part of the body part. In this case, the attachment may be performed by heat sealing or viscous sealing, but the present invention is not limited thereto.

As shown in FIG. 19, the disposable microstructure shooting device includes a main layer, a base layer, a protection layer, microstructures, and pillars. The microstructures may be injected to a desired skin depth, depending on the length of the pillars formed in the disposable system. The length and number of the pillars are not particularly limited, and the pillars may be manufactured in various manners according to a target region, a dose of a target injectable substance (for example, a drug), characteristics of the target injectable substance. The corresponding device is discharged after use since the device is a disposable system.

A method of manufacturing the disposable shooting device is as follows:

(a) Molds having a configuration included in the device, such as a protection layer, a main layer, pillars, and a guiding channel, are manufactured.

(b) A substance used in the disposable system, for example, PDMS, plastics, glass, or aluminum, is melted and put into the manufactured molds.

(c) When the added substance is solidified, the substance is separated from the molds to assemble a protection layer, a main layer, a pillar, a base layer, microstructures, a guiding channel (for example, an alignment guide), and a sealer.

The length, number and shape of the pillars are not limited, and the longer pillars are pierced deeper into the skin. The main layer is designed so that the pillars are not bent, and the microstructures may be separated more precisely when an end portion of each of the pillars is slightly inserted into the main layer. The base layer is manufactured between the main layer and the protection layer for the purpose of precise separation. As shown in FIG. 18, when a pressure is applied to the pillars, only the microstructures are separated, and then inserted into the skin. The base layer may be manufactured using a substance which is the same as or different from that of the microstructures. For example, the base layer may be manufactured using a mixture which aids to heal wounds. Meanwhile, the microstructures may be fabricated on the main layer with no base layer. The protection layer is a layer configured to protect the microstructures from external environments, and serves to fix the microstructures so that the microstructures cannot be separated together with the base layer when the microstructures are separated from the base layer. The alignment guide of FIG. 19 may be formed in the body part, or may be manufactured so that the alignment guide is included in the protection layer. FIG. 19 shows that the alignment guide is manufactured in a state in which the alignment guide is coupled to the protection layer. The alignment guide serves to aid to allow the pillars to exactly pass through the holes like the main layer. The sealing layer serves to protect the microstructures from contamination due to external environments and shield the entire system for long-term storage.

Advantageous Effects

The characteristics and advantages of the present invention are summarized, as follows:

(a) According to the present invention, the microstructures can be injected into the subject's skin in a painless and patchless manner.

(b) According to the present invention, many limitations of conventional biodegradable drug delivery systems can be overcome.

(c) For example, it takes approximately 2 hours to dissolve the microneedle, depending on the type of a substance constituting the microneedle in the case of the delivery of conventional patch-type biodegradable microneedle drugs. A target to be administered should wait until the microneedle is dissolved, and a patch should be then removed. According to the present invention, however, the microstructures can be injected into the skin within a time of less than one second, and the inconvenience of waiting for decomposition of the microstructures and removing a patch can be completely overcome.

(d) A significant number of people have an allergic reaction to an adhesive substance present in the patch. However, such a problem can be overcome since the present invention is embodied in a patchless manner. As described above, the microstructures and a very small portion of the base layer are injected into the skin. In this case, since the microstructures and the base layer are generally formed of a biocompatible substance, the microstructures and the base layer do not cause an allergic reaction.

(e) A conventional patch-type technique has a problem in that it is difficult to apply it to a hairy region, but such a problem can be completely overcome according to the present invention.

(f) According to the present invention, a depth of permeation of the microstructures into the skin can be precisely controlled by adjusting the pushing pressure.

(g) The present invention can open a new chapter in a percutaneous drug delivery system due to the convenience and elaboration (particularly, in adjusting a depth of permeation of the microstructures into the skin).

(h) According to the present invention, any microstructures fabricated with any substance can be injected into the skin, regardless of a method of fabricating the microstructures.

DESCRIPTION OF DRAWINGS

FIG. 4A shows that the holes of the main layer have the same size as the diameter of the bottom parts of the microstructures, FIG. 4B shows that the holes of the main layer have a smaller size than the diameter of the bottom parts of the microstructures, and FIG. 4C shows that the holes of the main layer have a larger size than the diameter of the bottom parts of the microstructures.

FIGS. 16A and 16B show graphs plotted for the insulin release profiles in the case of the DMN patch and when the microlancer is inserted into the hairless and hairy skins from dead pigs to a depth of 50 µm (blue, triangle marks) and 100 µm (red, square marks), respectively. The release profiles of the microlancer are observed regularly in two groups. On the other hand, a significantly low release profile of the patch is observed in the hairless skin. The lowest release profile is observed when the patch is inserted into the hairy skin. FIG. 16C shows insulin-loaded DMNs before application onto the hairless (see 'c') and hairy (see 'd') skin (upper panel) and after a lapse of 2 hours (lower panel). The DMNs in which insulin is loaded onto a patch are more slowly dissolved when applied to the hairy skin. e: A 3×3 array of insulin-loaded DMNs installed in a microlancer is shown (before application: upper panel, and after application: lower panel). The DMNs are completely separated from a CMC layer by the microlancer. Scale bar: 1 mm at c and d. Scale bar: 2 mm at e.

FIG. 17A shows diabetogenic mice before/after shaving (see 'a' and 'b'). Images of the diabetogenic mice obtained when the insulin-loaded DMNs are applied using the patch (see 'c') and the microlancer (see 'd') are shown. FIG. 17B is a graph plotted for changes in plasma glucose levels in diabetogenic mice over 6 hours. The lowest plasma glucose levels in the microlancer-treated mice are similar to those of the subcutaneous injection-treated mice although there is a one-hour gap between the two groups, which is expected that it takes a predetermined time to dissolve a DMN polymer. FIG. 17C shows the plasma insulin concentrations in the mice of each group over time.

FIG. 20 is a schematic view showing a coupling structure of microstructures included in a top part of the disposable microlancer of the present invention. A base layer may be manufactured with or without holes.

EMBODIMENTS

Hereinafter, the present invention will be described in further detail with reference to embodiments. However, it should be understood that the description proposed herein is just a preferable example for the purpose of illustrations only, not intended to limit the scope of the invention, so it will be apparent to those skilled in the art that other equivalents and modifications could be made thereto without departing from the scope of the invention.

EXAMPLES

Example 1: Manufacture of Shooting Microneedle Structure

Figure 1A:
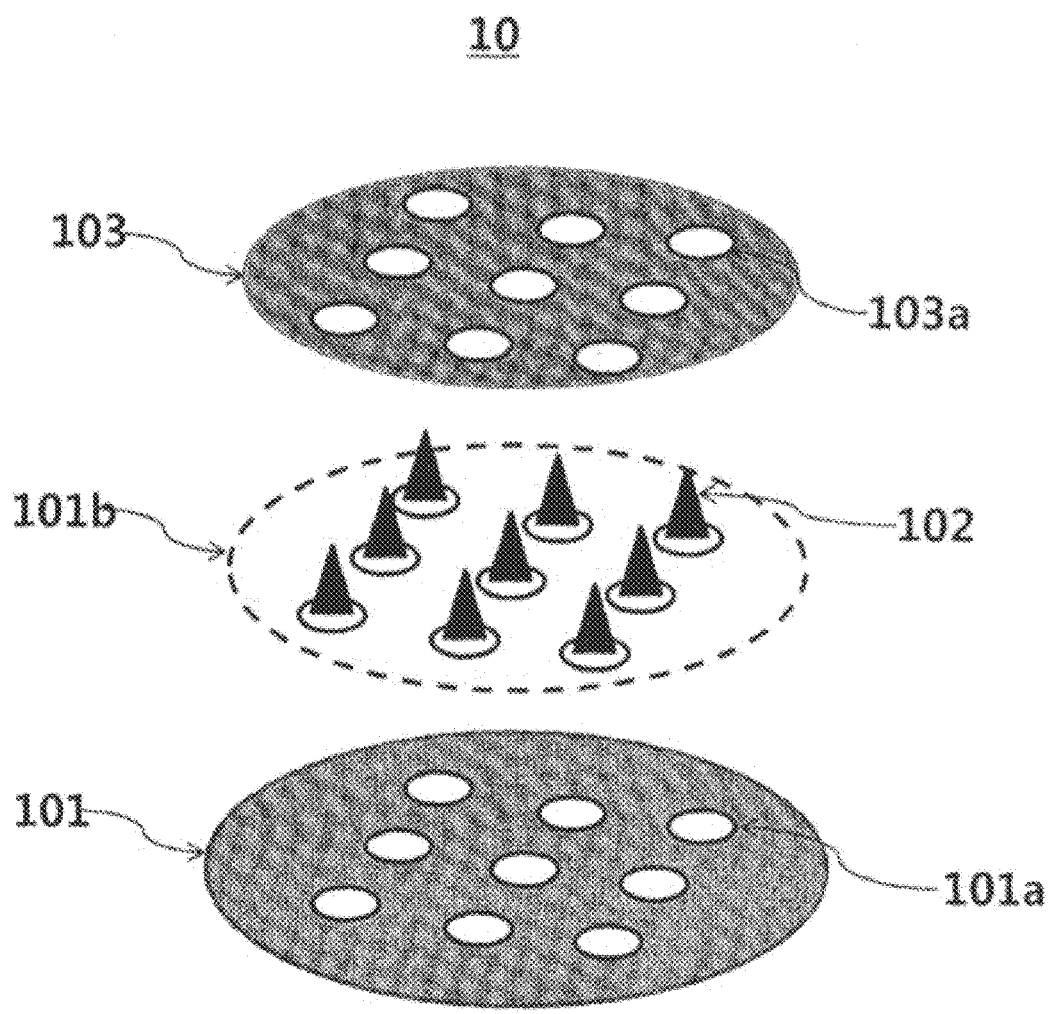
FIG. 1A is a schematic view of a shooting microstructure I of the present invention. 10: shooting microstructure I, 101: main layer, 101a: holes of main layer, 101b: surface of main layer, 102: microstructures (for example, microneedles), 103: protection layer, 103a: holes of protection layer.
Figure 1B:
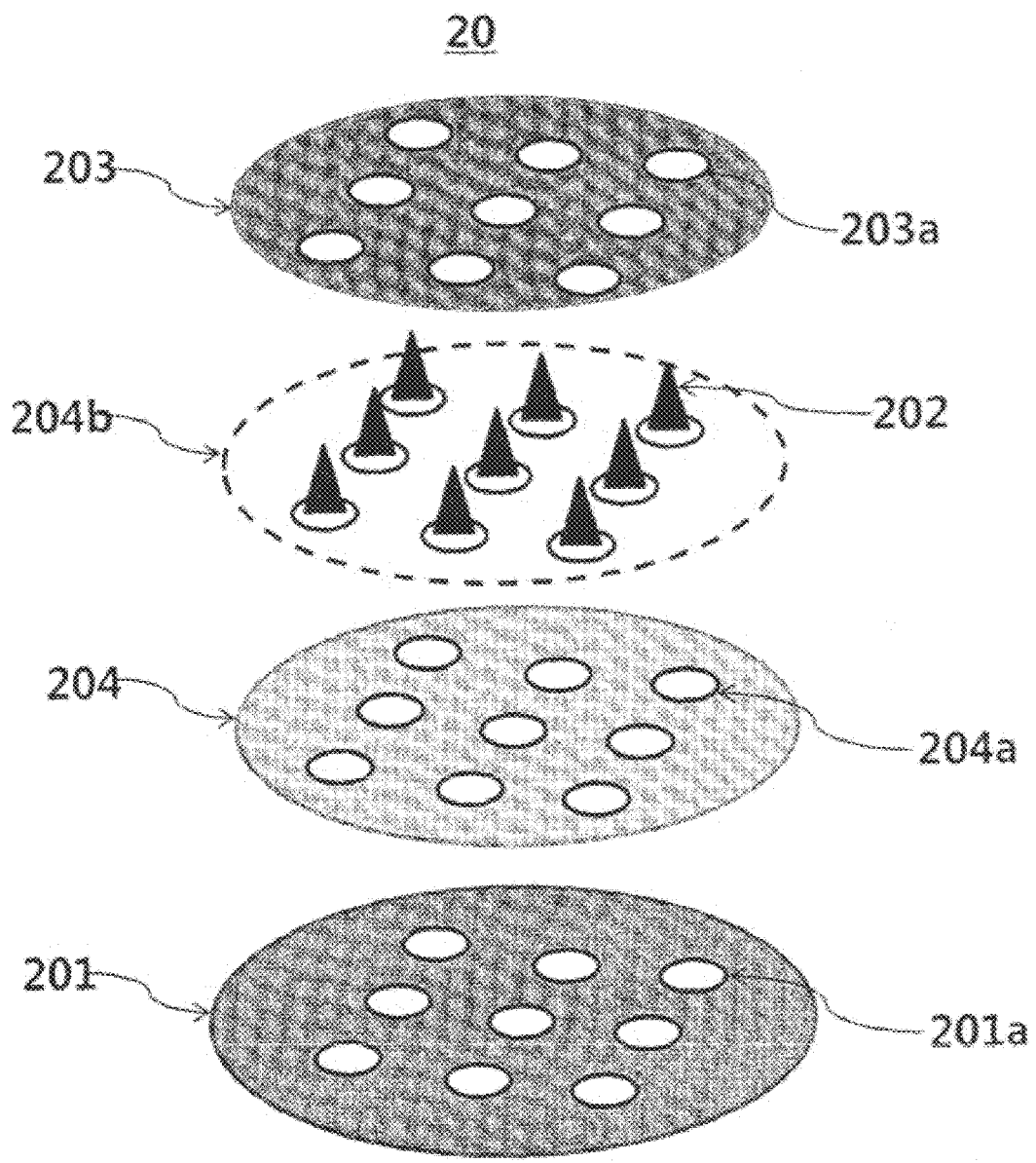
FIG. 1B is a schematic view of a shooting microstructure II of the present invention. 20: shooting microstructure II, 201: main layer, 201a: holes of main layer, 202: microstructures (for example, microneedles), 203: protection layer, 203a: holes of protection layer, 204: base layer, 204a: holes of base layer.
Figure 1C:
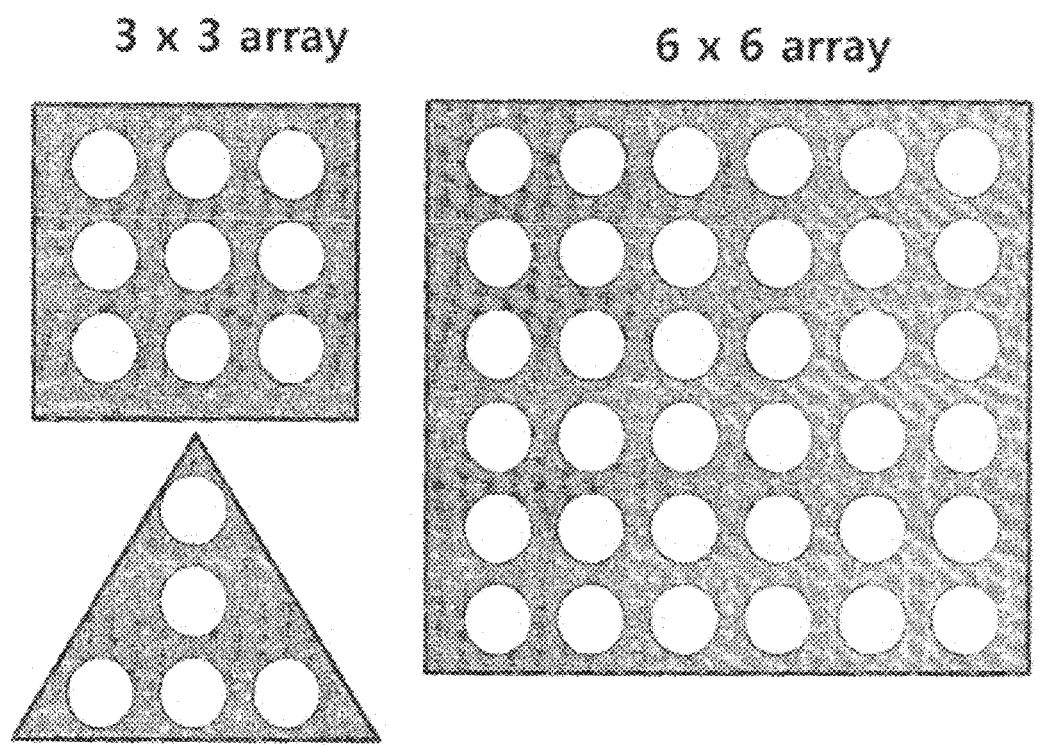
FIG. 1C shows various examples of hole arrays that may be formed in the shooting microstructure of the present invention.

FIGS. 1A and 1B are diagrams showing shooting microneedle structures according to the present invention. As shown in FIGS. 1A and 1B, holes may be introduced by various methods so that a main layer has a diameter of 3.5 cm, a protection layer has a diameter of 3.5 cm, and the holes have a diameter of 500 µm. Biodegradable shooting microneedles fabricated thus may be fabricated in two shapes. In this Example, microstructures formed on a main layer 101 and on a surface 101b of the main layer (a shooting microstructure I) and microstructures formed on a base layer 204 (a shooting microstructure II) were manufactured. Thereafter, a viscous biocompatible polymer was extended by the method disclosed in Korean Patent No. 0793615 previously filed by the present inventors and the method disclosed in Korean Unexamined Patent Application Publication No. 2013-0019247, thereby fabricating microstructures. During a process of preparing such a viscous biocompatible polymer, a biocompatible substance was mixed with a drug so that the resulting mixture could be percutaneously administered using the microstructures.

Figure 2:
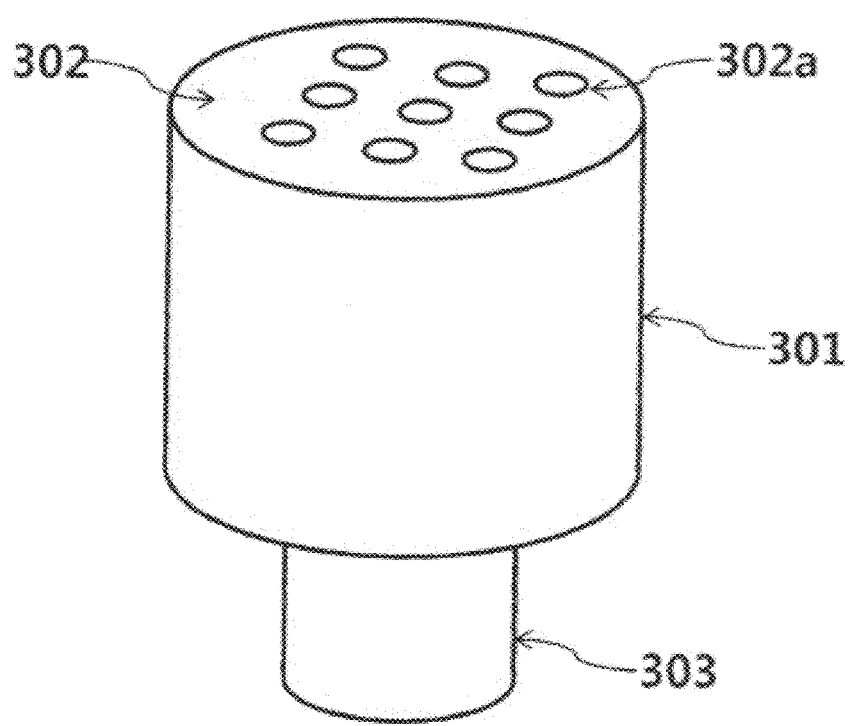
FIG. 2 is a schematic view of a microstructure shooting device of the present invention. 30: shooting device, 301: body part, 302: top part, 302a: holes of top part, 303: connection part.
Figure 3:
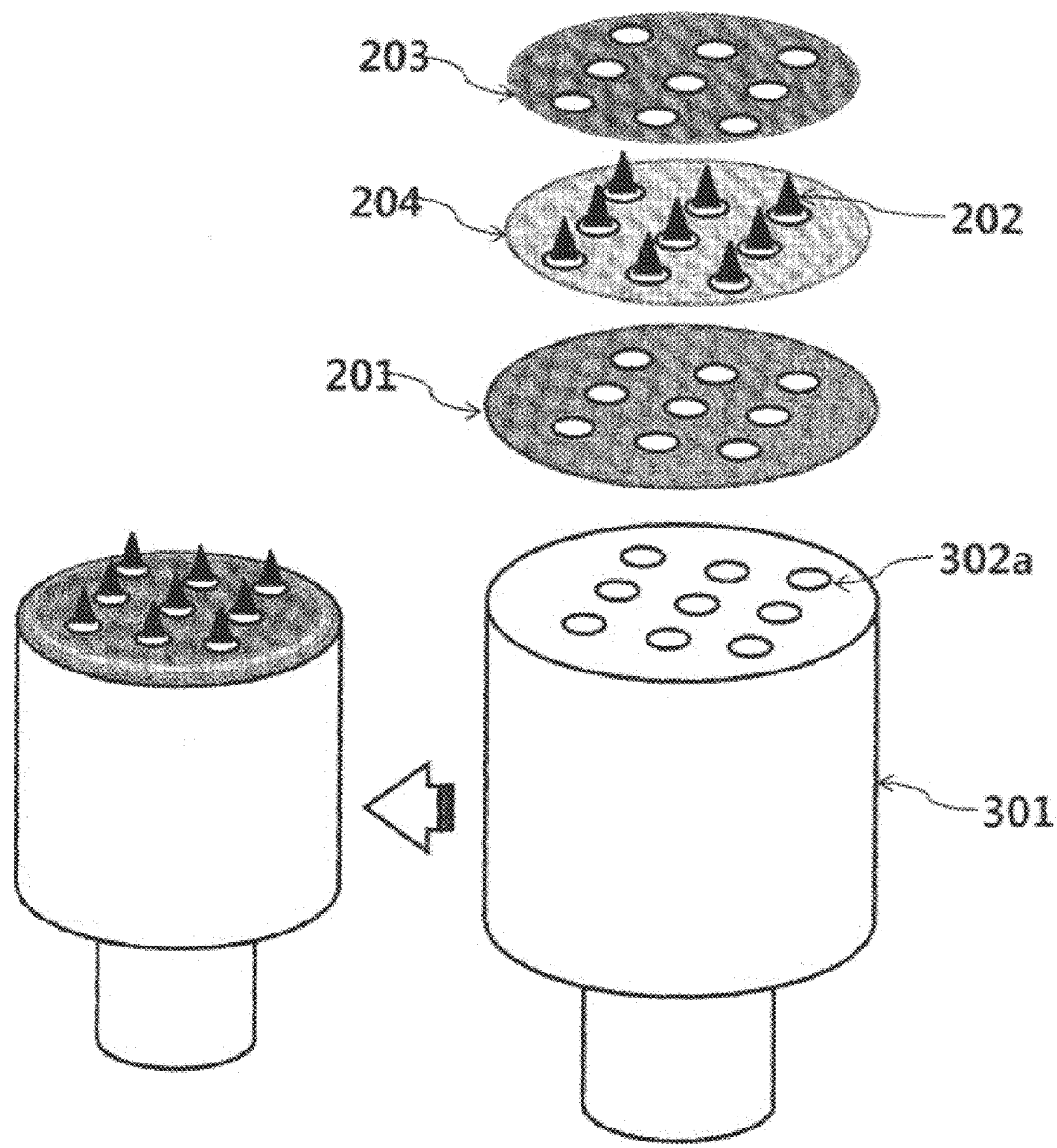
FIG. 3 is a schematic view of a shooting device coupled to the shooting microstructure II.

FIGS. 2 and 3 are diagrams showing a shape of a microstructure shooting device 30 according to the present invention, and the microstructure shooting device coupled to the microstructure. As shown in FIG. 2, a plurality of holes 302a were formed on a top part of the shooting device, and the shooting device 30 includes a top part 302 configured to accommodate the shooting microstructure, and has a structure in which the shooting microstructure is attached to the top part 302. The shooting device 30 further includes a pushing pressure generation unit configured to apply a pushing pressure to a pushing pressure transmission channel. Therefore, when a body part 301 including the pushing pressure transmission channel is provided with the pushing pressure generation unit, a pushing pressure is transmitted to the plurality of holes to separate microneedles from the structure and shoot the microneedles. As a result, the shooting microstructure was manufactured so that the microneedles are inserted into the skin.

Figure 4A:
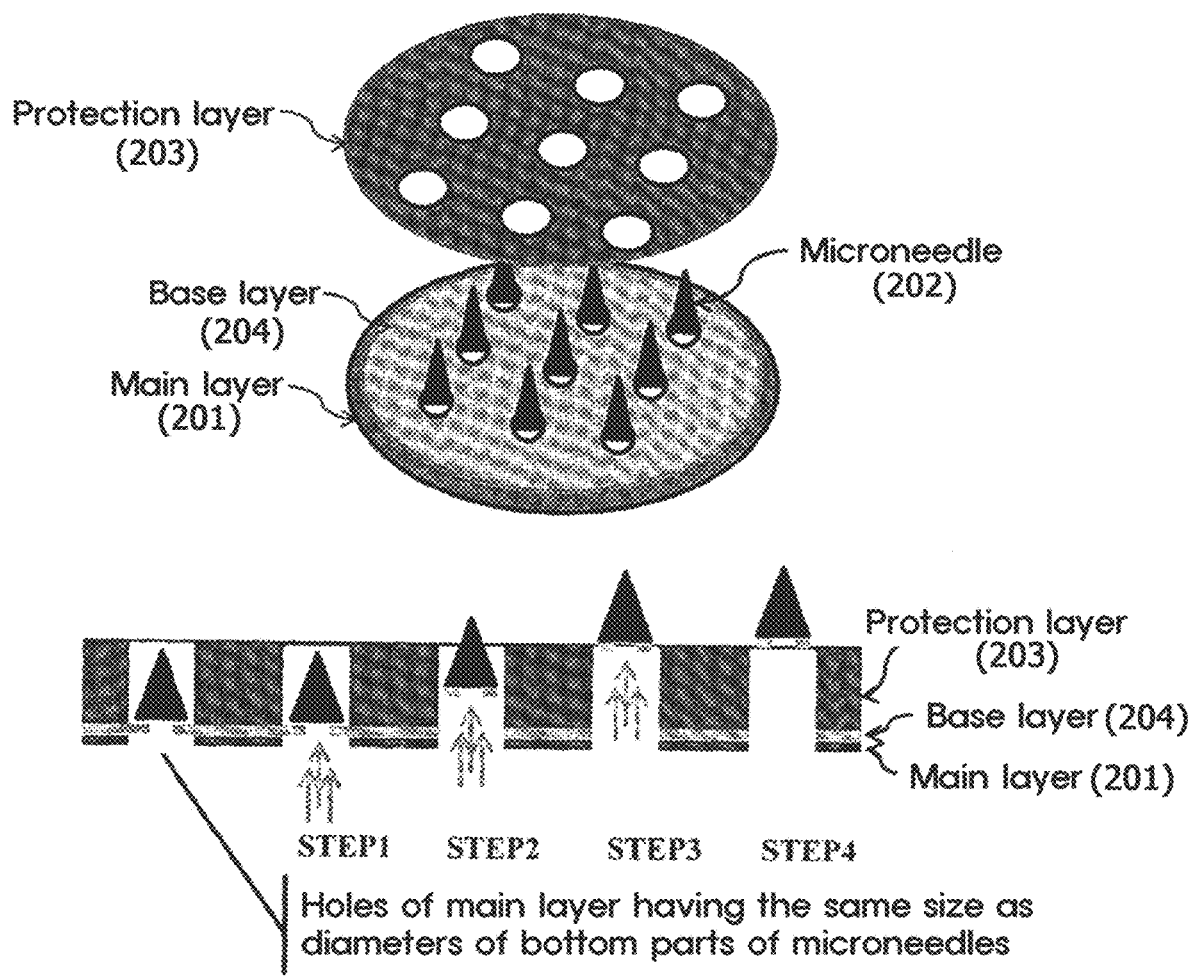
FIGS. 4A to 4C are schematic view showing methods of shooting the microstructures, depending on the size of the holes of the main layer and the diameter size of bottom parts of the microstructures (for example, microneedles).
Figure 4B:
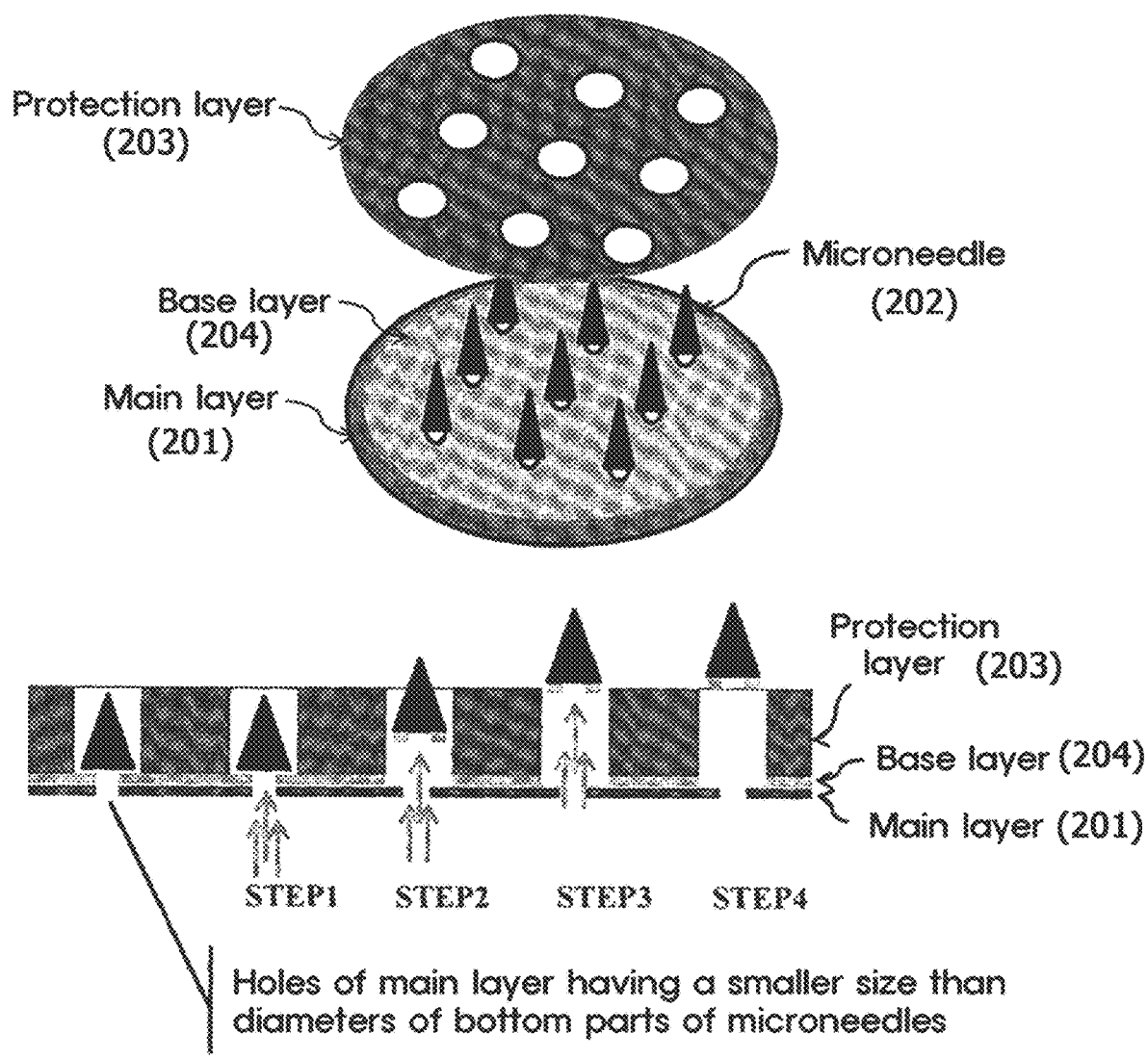
Figure 4C:
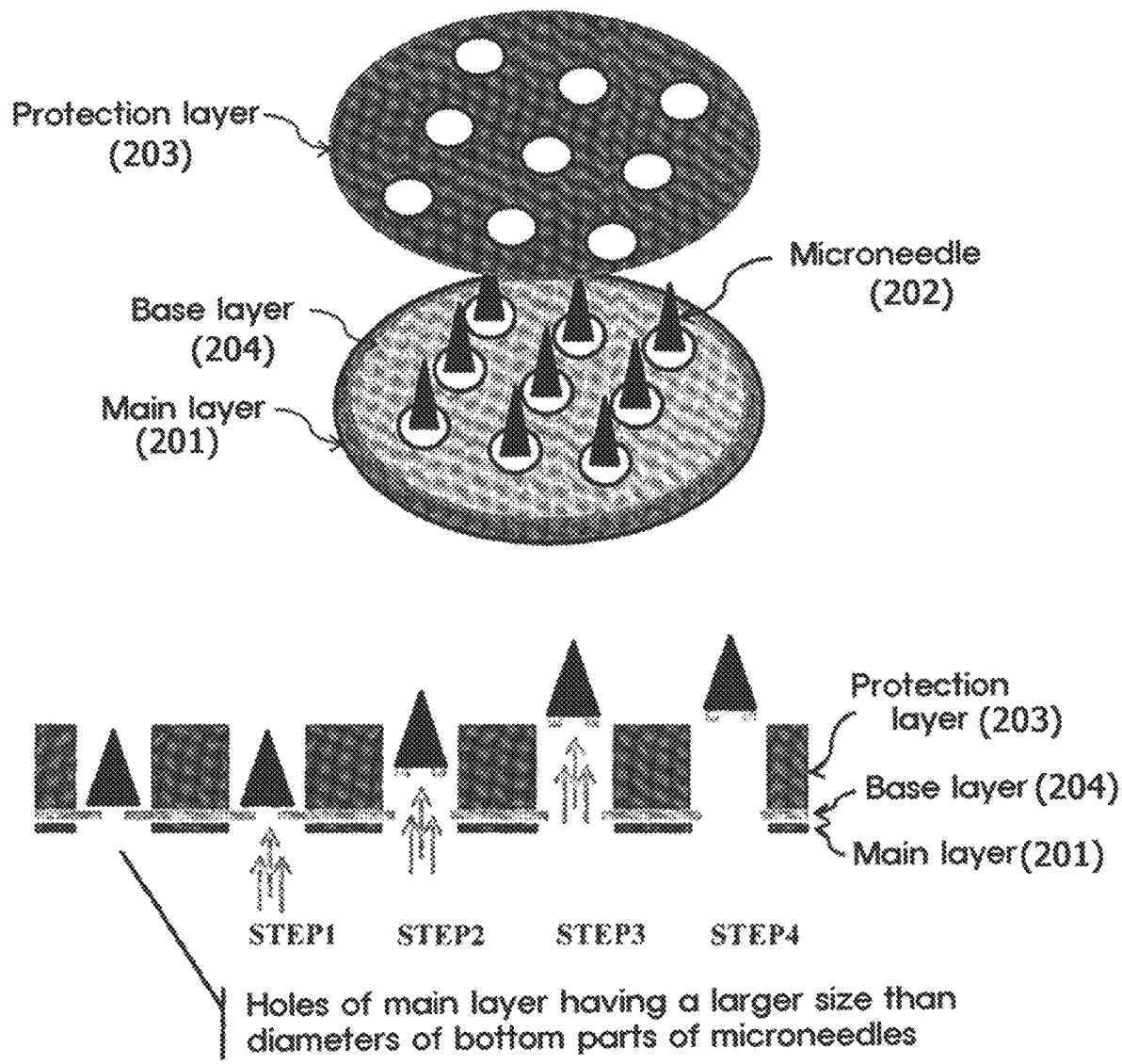

As described in detailed with reference to FIGS. 4A, 4B and 4C, the configuration and operation of the biodegradable microstructure according to the present invention are as follows. FIG. 4A shows a case in which the holes of the main layer have the same size as the diameter of bottom parts of the microstructure, FIG. 4B shows a case in which the holes of the main layer have a smaller size than the diameter of bottom parts of the microstructure, and FIG. 4C shows a case in which the holes of the main layer have a larger size than the diameter of bottom parts of the microstructure.

Figure 5:
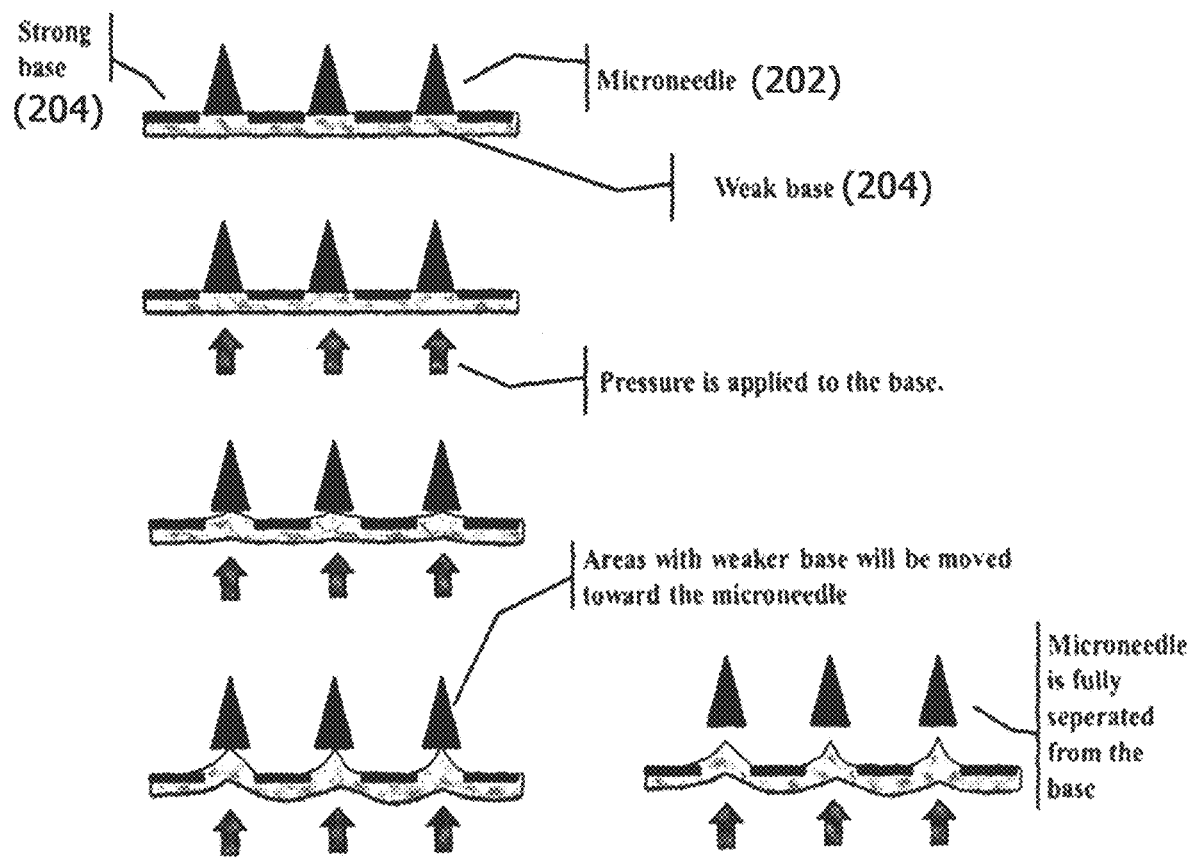
FIG. 5 shows one embodiment in which weak and strong pattern coating is applied to the present invention. Regions of the base layer on which the microstructures are fabricated have a weaker strength than the other regions of the base layer.

FIG. 5 is a diagram showing a principle in which weak and strong pattern coating is applied to the present invention. Regions of the base layer on which the microstructures were fabricated had a weaker strength than the other regions of the base layer. As a result, the shooting microstructure was manufactured so that the microstructures were easily separated from weaker regions of the base layer to be shot when a pushing pressure was applied to bottom parts of the microstructures.

FIGS. 6, 7, 8 and 9 show various methods of shooting the shooting microstructure.

Figure 6A:
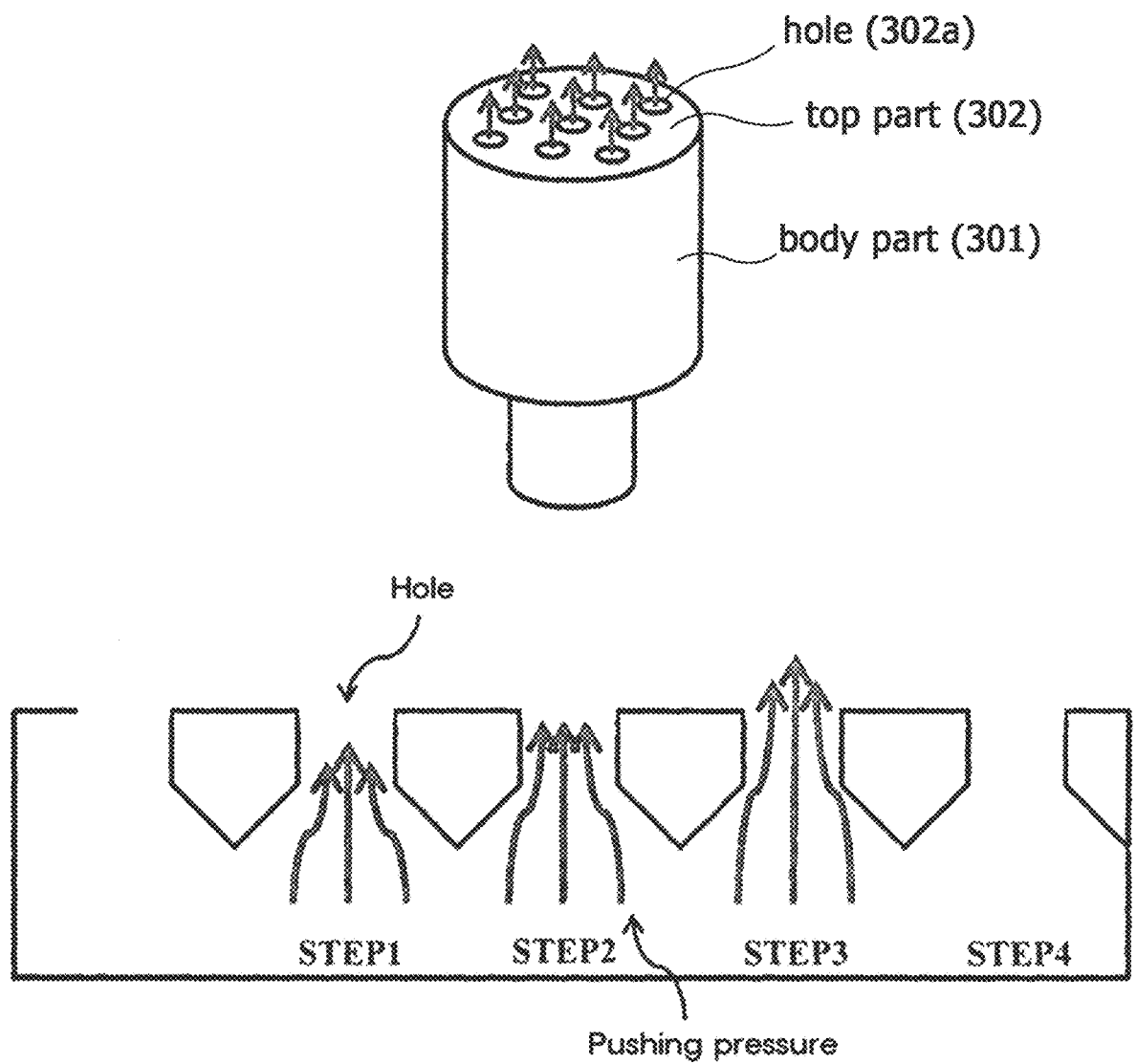
FIGS. 6A and 6B show one embodiment in which a pushing pressure is transmitted to the microstructures according to the present invention. The pushing pressure generated by a pushing pressure generation unit is transmitted to the microstructure through a plurality of holes formed in a top part of the shooting device, thereby shooting the microstructures.
Figure 6B:
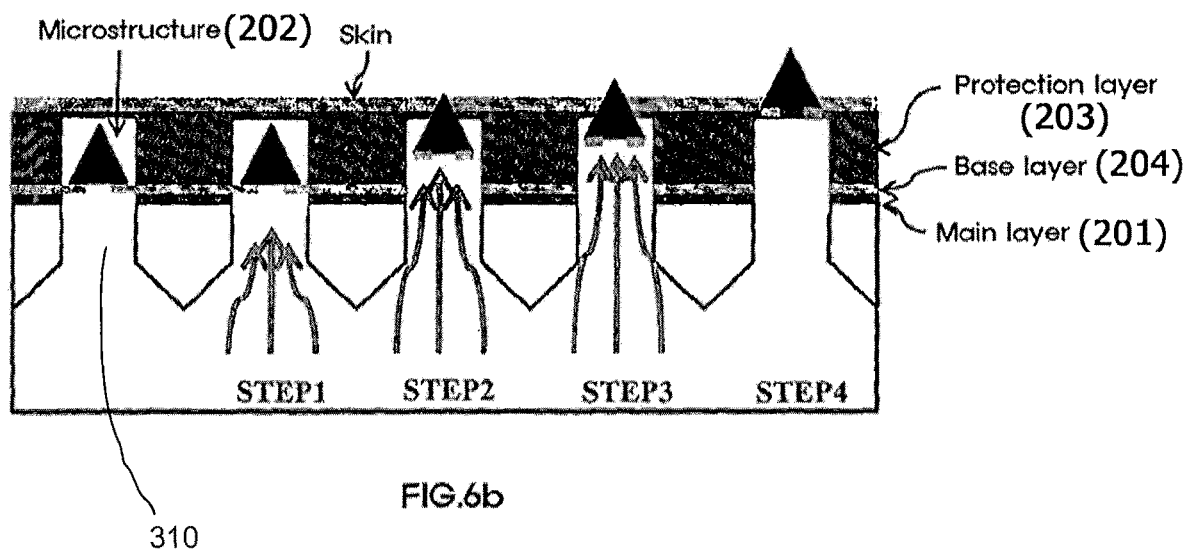

FIGS. 6a and 6b are diagrams showing a configuration and an operation method of a biodegradable shooting microneedle device according to the present invention. As shown in FIGS. 6a and 6b, the shooting microneedle device included a top part 302 having a diameter of 3.6 cm and having holes 302a formed therein, and was manufactured so that bottom parts of the shooting microstructures 102 or 202 were arranged at the same position as the holes. In this experiment, the size of the holes was 500 μm, and the diameter of the pillars was 495 μm. In this case, the shooting microneedle device was manufactured so that a pushing pressure generated by the pushing pressure generation unit was transmitted via pushing pressure transmission channels 310 to bottom parts of the microstructures 102 or 202 through the plurality of holes 302a formed in the top part 302 of the shooting device 30, and thus the microstructures 102 or 202 were shot to deliver a drug into a human body.

Figure 7A:
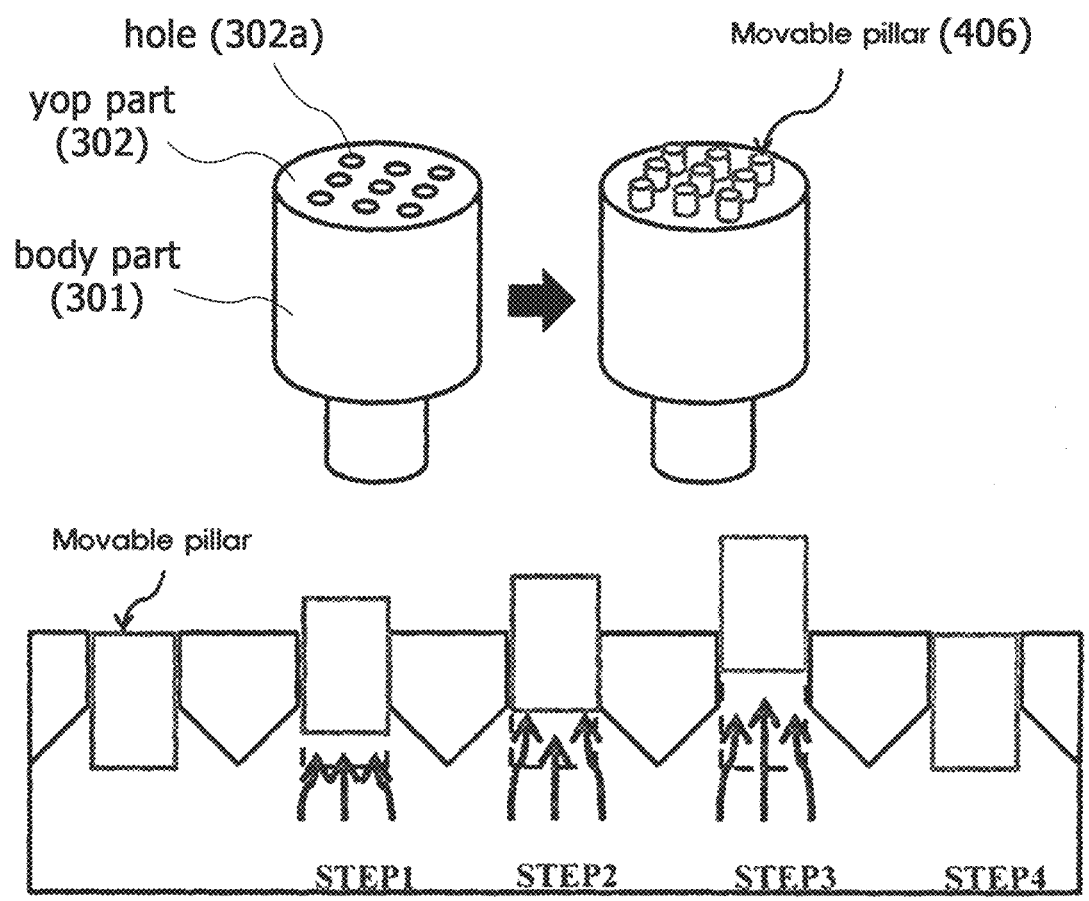
FIGS. 7A and 7B show another embodiment in which a pushing pressure is transmitted to the microstructures according to the present invention. When movable pillars that may be input/output into/from the holes move forwards, the pushing pressure is transmitted to bottom parts of the microstructures, thereby shooting the microstructures.
Figure 7B:
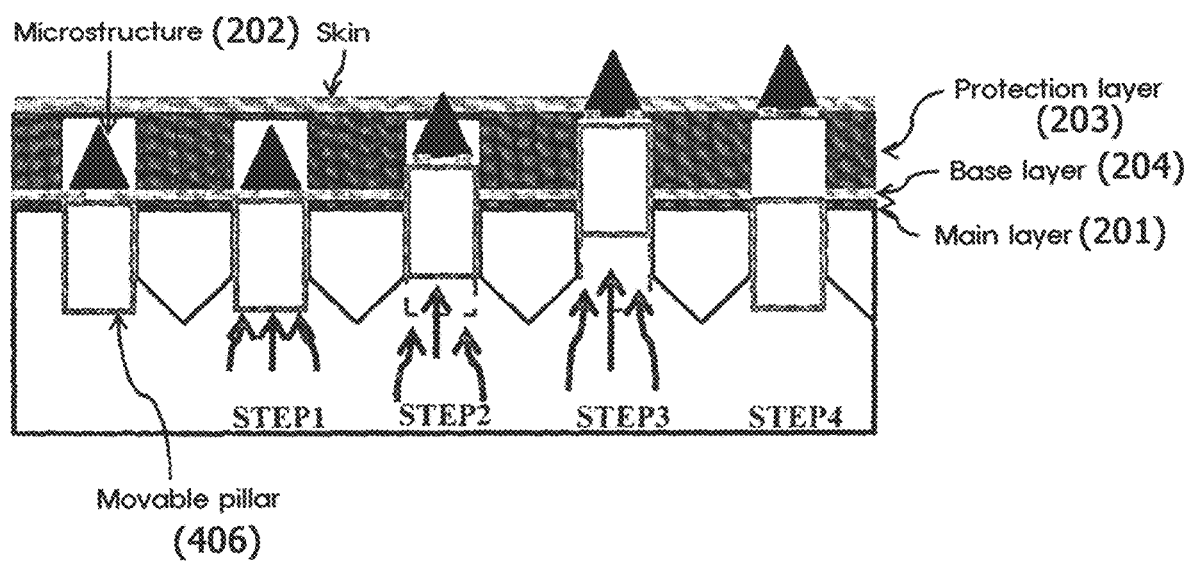

FIGS. 7A and 7B are diagrams showing a configuration and an operation method of a biodegradable shooting microneedle device according to the present invention. As in a configuration shown in FIG. 7A, the shooting device 30 further includes movable pillars arranged inside a pushing pressure transmission channel. The shooting microneedle device was manufactured so that, as a pushing pressure generated by the pushing pressure generation unit was applied so that the movable pillars that may be input/output into/from the holes moved forwards, the microstructures were separated, and shot to be inserted into the skin, thereby delivering a drug into a human body.

Referring to FIGS. 6b and 7b, the base layer 204 includes a portion (microstructure region) underneath a microstructure 204 and another portion (no-microstructure region) over which no microstructure is formed. The left two illustrations of FIGS. 6b and 7b, the microstructure region and no-microstructure region next thereto are continuous to provide a unitary layer for the base layer 204. In the other illustrations (STEPS 2-4) of FIGS. 6b and 7b, the microstructure region of the base layer 204 is separated from the no-microstructure region as the microstructure immediately over the microstructure region moves, and the microstructure region separated from the no-microstructure region travels together with the microstructure.

Figure 8A:
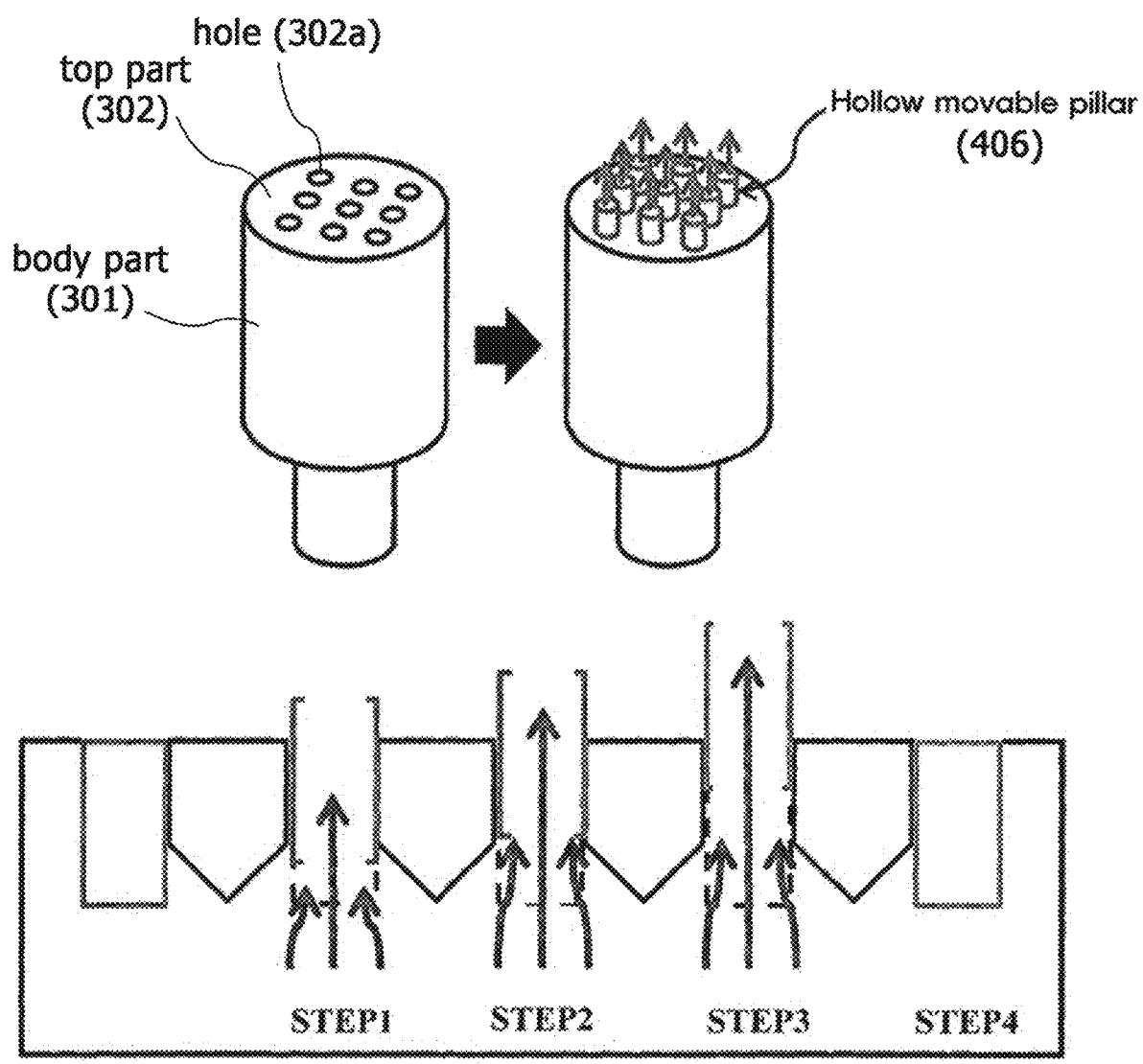
FIGS. 8A and 8B show still another embodiment in which a pushing pressure is transmitted to the microstructures according to the present invention. When the movable pillars that may be input/output into/from the holes move forwards, the pushing pressure is transmitted to bottom parts of the microstructures, thereby shooting the microstructures. Thereafter, when an air pressure is applied through holes of the pillars, the microstructures move deeper into the skin. Optionally, the pushing pressure caused by the pillars and the pushing pressure caused by the air through the holes may be applied at the same time so that the microstructures are pierced into the skin.
Figure 8B:
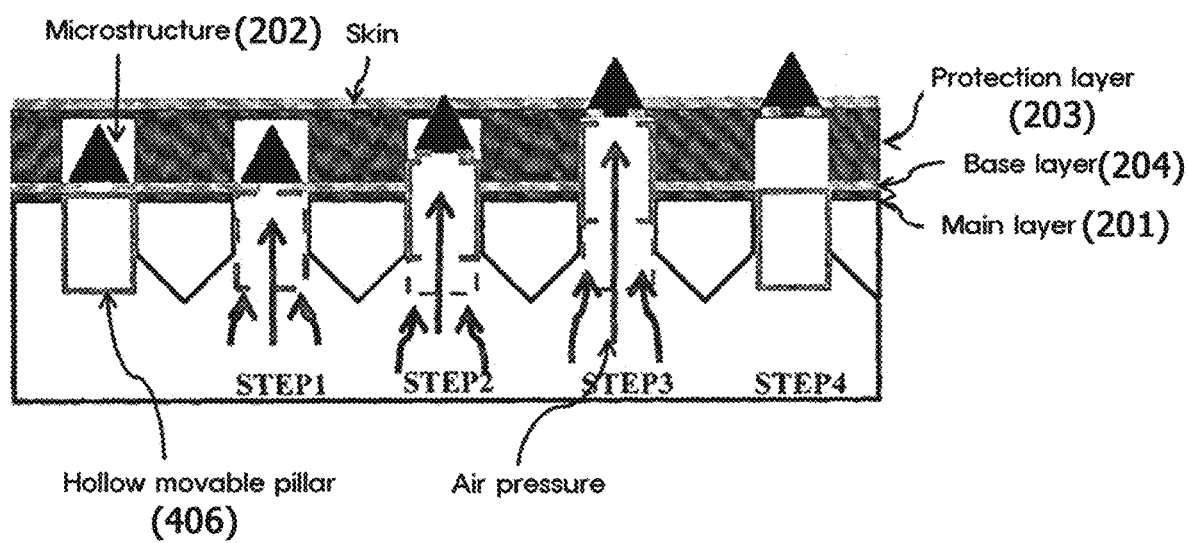

FIGS. 8A and 8B are diagrams showing another configuration and operation method of a biodegradable shooting microneedle device according to the present invention. This method is a combination of the first and second methods, and the biodegradable shooting microneedle device includes hollow movable pillars, as shown in FIG. 8A. FIG. 8B is a diagram showing an operation of the microstructure device including the hollow movable pillars according to the present invention. The biodegradable shooting microneedle device was manufactured so that a pushing pressure was transmitted to the bottom part of the shooting microstructure through the holes when an air pressure was applied through the holes of the movable pillars, and the microstructures moved deeper into the skin while being separated and shot when a pressure was applied to the shooting microstructure 10 or 20 by means of the movable pillars, thereby delivering a drug into a human body.

Figure 9A:
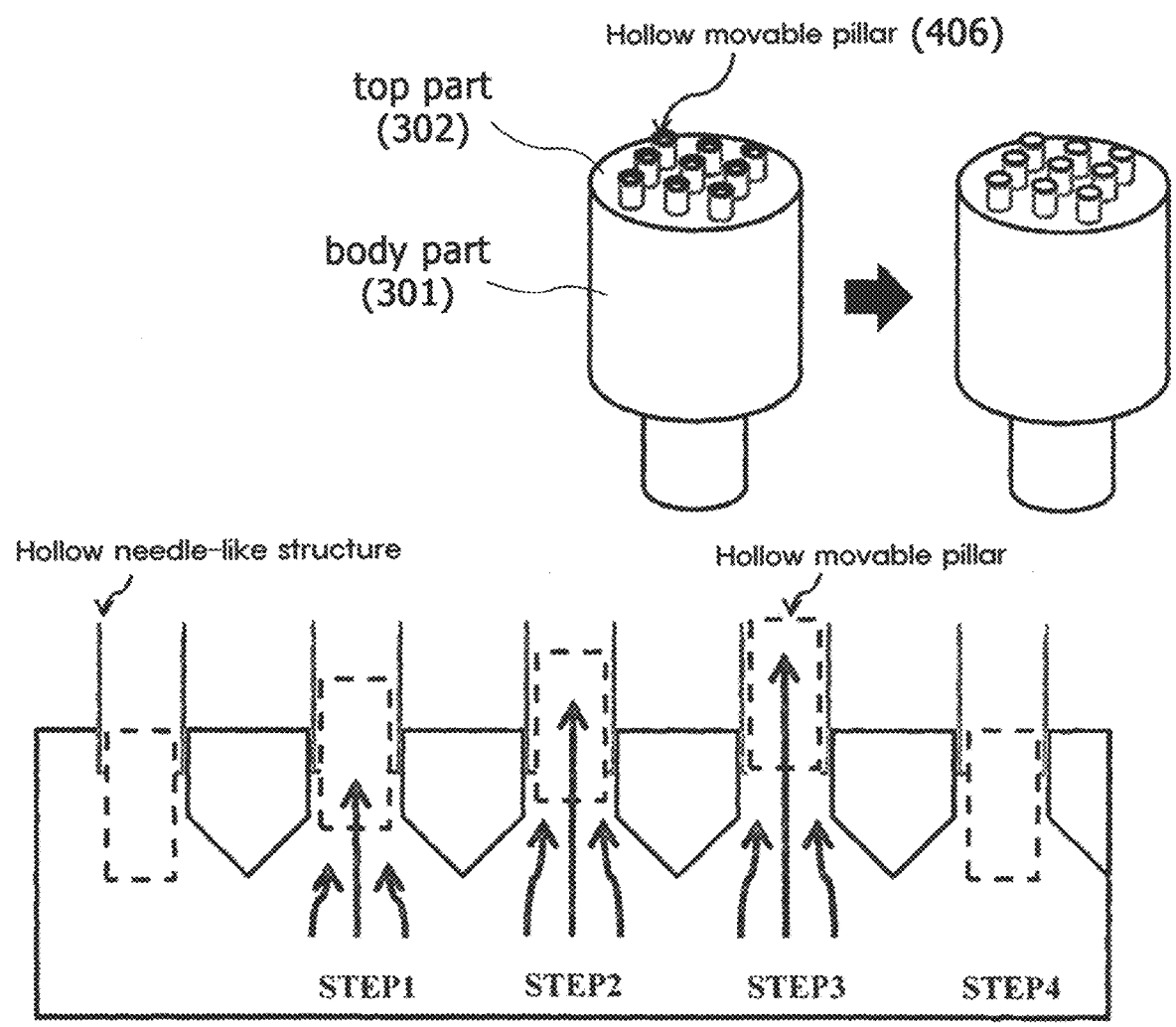
FIGS. 9A and 9B show yet another embodiment in which a pushing pressure is transmitted to the microstructures according to the present invention. The shooting microstructure includes a hollow needle-like structure. The hollow needle-like structure is pierced into the skin, and hollow movable pillars allow the microstructures to be pierced into the skin. When the movable pillars that may be input/output into/from the holes move forwards, the pushing pressure is transmitted to bottom parts of the microstructures, thereby shooting the microstructures. Thereafter, when an air pressure is applied through holes of the pillars, the microstructures move deeper into the skin. Optionally, the pushing pressure caused by the pillars and the pushing pressure caused by the air through the holes may be applied at the same time so that the microstructures are pierced into the skin.
Figure 9B:
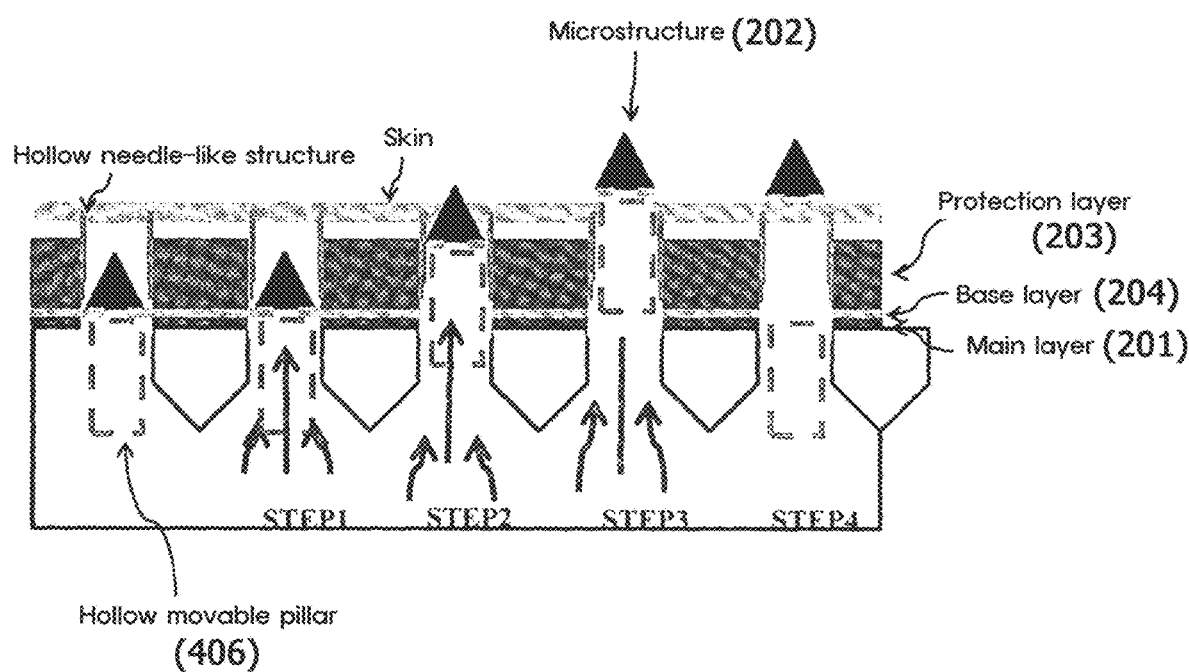

FIGS. 9A and 9B are diagrams showing still another configuration and operation method of a biodegradable shooting microneedle device according to the present invention. As shown in FIG. 9, the device was manufactured in a similar fashion to include hollow movable pillars, as described in the shooting microneedle device shown in FIG. 8A, but was manufactured to operate in a different manner. FIG. 9A is a diagram showing a microstructure device including hollow movable pillars into which the microstructures according to the present invention are inserted. As specifically shown in FIG. 9B, an operation of the microstructures according to the present invention is as follows. When the shooting microstructure 10 or 20 was manufactured, the hollow movable pillars including the microstructures 101 or 202 were arranged in holes of the shooting microstructure 10 or 20. Then, when a pushing pressure was applied, the pushing pressure stimulated weaker regions of the base layer, and thus the microstructures were separated together with the hollow movable pillars, and shot to lose elasticity of the skin and pierce the skin. Subsequently, the device was manufactured so that the microstructures were separated from the hollow movable pillars to deliver a drug into a human body.

Example 2: Percutaneous Injection of Shooting Microstructure Using Microlancer

Humalog insulin used in this experiment was purchased from Eli Lilly. Low-viscosity carboxymethyl cellulose (90 kDa) and streptozotocin (N-(methylnitrosocarbamoyl)-α-D-glucosamine) were purchased from Sigma-Aldrich. Sodium hyaluronate (HA, 39 kDa) was purchased from Soliance. An acrylamide solution (40%), ammonium persulfate and N,N,N',N'-tetramethylethylenediamine (ReagentPlus, 99% purity) were purchased from Sigma-Aldrich. Tris and sodium dodecyl sulfate (SDS) were purchased from Amresco. A green dye was purchased from Bowon.

Manufacture of Dissolving Microneedles (DMNs):

10% CMC powder was mixed with distilled water and 0.2 IU of insulin to prepare an insulin-loaded viscous CMC polymer. An insulin-CMC solution was dispensed onto holes (diameter: 500 μm). The holes were aligned in a 3×3 array on an automated X, Y and Z stage (SHOT mini 100-s, Musashi). Thereafter, the insulin-CMC solution was extended at a rate of 3 mm/min for 17 seconds to fabricate microneedles. The DMNs formed in the holes had a height of 600 μm and a tip diameter of 10±5 μm. The same method was applied to fabricate DMNs of hyaluronic acid (HA). Simply, a HA powder was mixed with distilled water to prepare a viscous solution, and a 0.1% green dye was added to the HA polymer solution. Then, this final solution was used to fabricate DMNs. The mechanical strength of the DMNs thus fabricated was measured to be 0.498±0.020 N [Zwick Z0.5 TN; Zwick GmbH & Co].

Video Imaging:

DMNs were inserted into 20% polyacrylamide gel using a microlancer. Insertions of DMNs to depths of 50 μm and 2.5 mm were recorded using a high-speed video camera (Phantom V710).

Experiment for Measuring In Vitro Insertion Depth:

A microlancer was used to visualize a depth of insertion of green dye-loaded DMNs into hairy and hairless skins from dead pigs. The DMNs were inserted to target depths of 50 μm, 100 μm and 300 μm. The insertion depths obtained in the hairless and hairy skins were compared, and histologically evaluated using a microscope. For analysis, tissue samples of the hairy and hairless skins from the dead pigs for insertion to depths of 50 μm, 100 μm and 300 μm were embedded in an OCT compound, and microtomed to 25-μm-thick sections. The sections were stained with hematoxylin, and then stained with eosin. The stained sections were dehydrated with alcohol, cleaned with xylene, and then mounted on PERMOUNT (mounting medium) (Fisher Scientific).

In Vitro Insulin Delivery Profiling:

Release profiles of DMNs loaded with 0.2 IU insulin in skins from dead pigs were examined using Franz diffusion cells (Hanson). Diffusion cells were filled with 7 ml PBS, and mixed using a magnetic stirrer before experiments. Each of hairy and hairless regions from the back skin of a pig was cut at a size of 1 cm$^3$, and then loaded on a receptor filled with PBS. Thereafter, a DMN patch was inserted into each skin fragment, and a pressure was applied onto the skin using an empty donor chamber. Then, the DMN patch was fixed using a pinch clamp (n=3). Meanwhile, DMNs inserted into the respective skins (to a depth of 50 μm) using a microlancer were treated in the same method (n=3). After 10, 20, 30, 60 and 120 minutes of the insertion, 0.5-ml-thick samples were taken from the receptor, and the content of insulin was measured using an ELISA kit (ALPCO). After eleven samples were taken, each sample ware exchanged with an equivalent volume of a buffer. All the samples were stored at −10° C. before analysis.

Insulin-Loaded DMN Stability Study:

Insulin-loaded DMNs were dissolved in 1 ml of PBS (pH 7.4), and insulin was quantified using an ultra-performance liquid chromatography (UPLC; ACQUITY UPLC I-Class, Waters). In the UPLC system, a TUV detector and a 2.1×100 mm column were used (Acquity, Waters). A mobile-phase system was composed of (A) 0.1% trifluoroacetic acid (TFA) in DW and (B) TFA in acetonitrile (75:25 ratio). The system was set to a column temperature of 35° C., a flow rate of 0.250 mL/min, and compounds in an eluent was measured using a UV detector at 214 nm. The standard calibration curve was plotted in an insulin concentration range of 0 IU to 1.5 IU. The areas of an insulin peak curve before/after DMN fabrication were compared.

Diabetic Animal Model:

In this experiment, male C57BL/6 mice (7 to 8 week-old, OrientBio) were used. Animal experiments were conducted according to the Guide for the Care and Use of Laboratory Animals by the Severance Hospital Ethics Committee (Reference No.: 09-013, College of Pharmacy, Yonsei University, Korea). The mice were anesthetized with Avertin (2,2, 2-tribromoethanol, Sigma-Aldrich), and 50 mg/kg of streptozotocin in a sodium citrate buffer (pH=4.5) was intravenously injected into the mice to induce diabetes. For successful diabetes induction, the blood glucose concentrations of all the mice were measured using a OneTouch Verio IQ system. As a result, it was revealed that the blood glucose concentrations were greater than or equal to 300 mg/dl.

In Vivo Delivery Efficiency Test:

Diabetogenic mice were divided into four groups, as follows: (a) an untreated group (a negative control); (b) a subcutaneously injected group (0.2 IU, a positive control); (c) a patch-treated group (0.2 IU insulin-loaded DMNs); and (d) a microlancer-treated group (0.2 IU insulin-loaded DMNs) (n=5 per group). The mice were fasted during an experiment period, and freely fed with water. The back regions of the mice were shaved using an electric shaver, and 0.2 IU of insulin was administered by means of a DMN patch through a microlancer or by subcutaneous injection. After 6 hours of the treatment, blood samples (0.1 ml) were taken from wounded tail vein areas every one hour. The blood samples were centrifuged at 10,000 rpm for 15 minutes to separate plasma. The serum samples were immediately frozen, and stored at −80° C. before analysis. The plasma glucose levels per hour in each group were measured using a glucose CII-Test kit. The plasma insulin concentrations were measured using an insulin ELISA kit (ALPCO).

Figure 10:
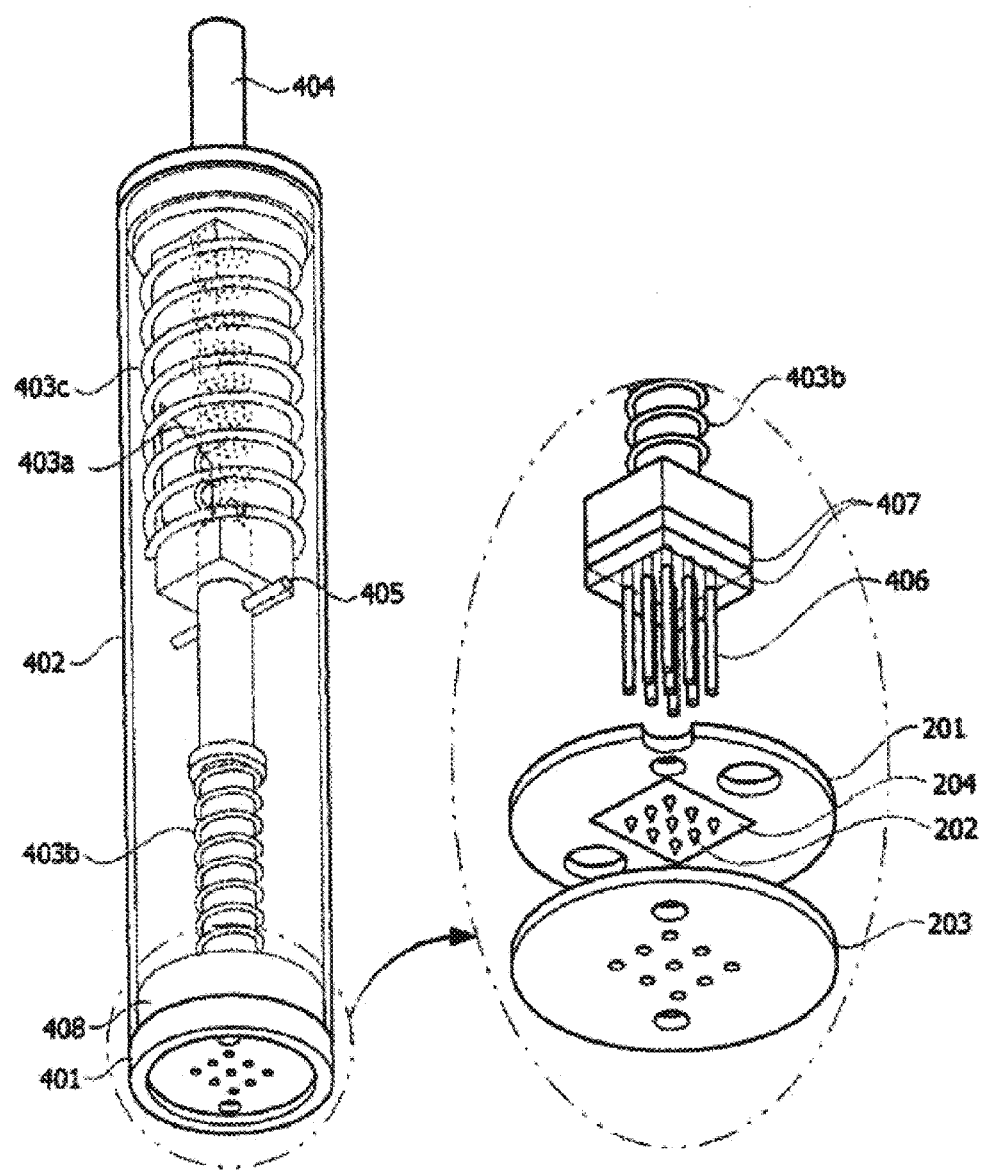
FIG. 10 is a schematic view of a microlancer of the present invention. 40: shooting microlancer, 201: main layer, 202: microstructures (for example, microneedles), 203: protection layer, 204: base layer, 401: top part, 402: body part, 403a: inner injecting spring, 403b: extracting spring, 403c: outer extracting spring, 404: button, 405: pin, 406: pillar, 407: spacer, 408: aligner.
Figure 11:
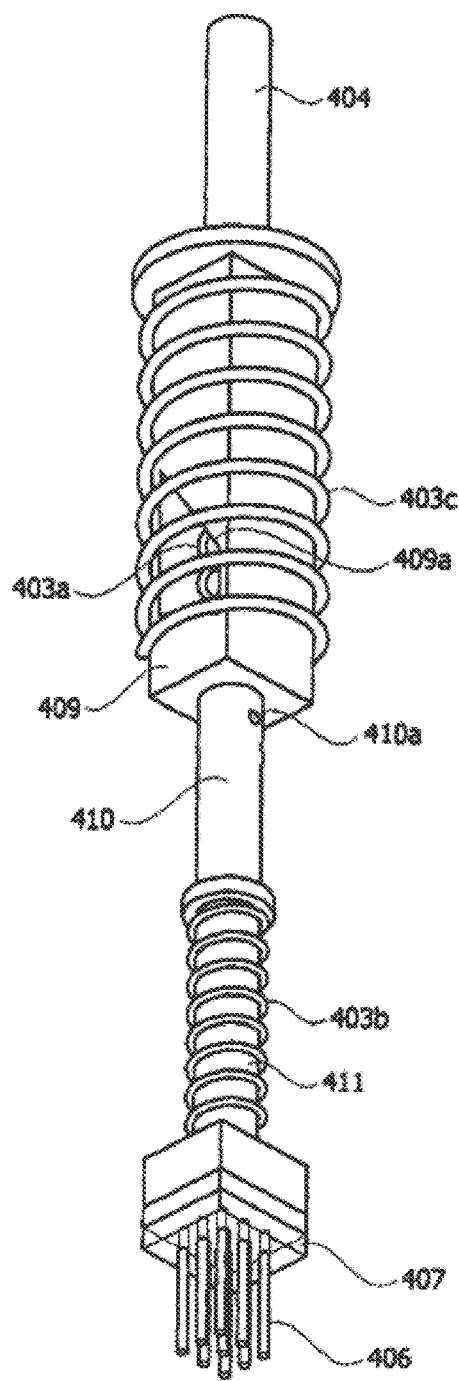
FIG. 11 is a schematic view of an inner configuration of the microlancer of the present invention. 403a: inner injecting spring, 403b: extracting spring, 403c: outer extracting spring, 404: button, 406: pillar, 407: spacer, 409: auxiliary pipe, 409a: slope, 410: connection pipe, 410a: pin hole, 411: connection pipe.
Figure 12:
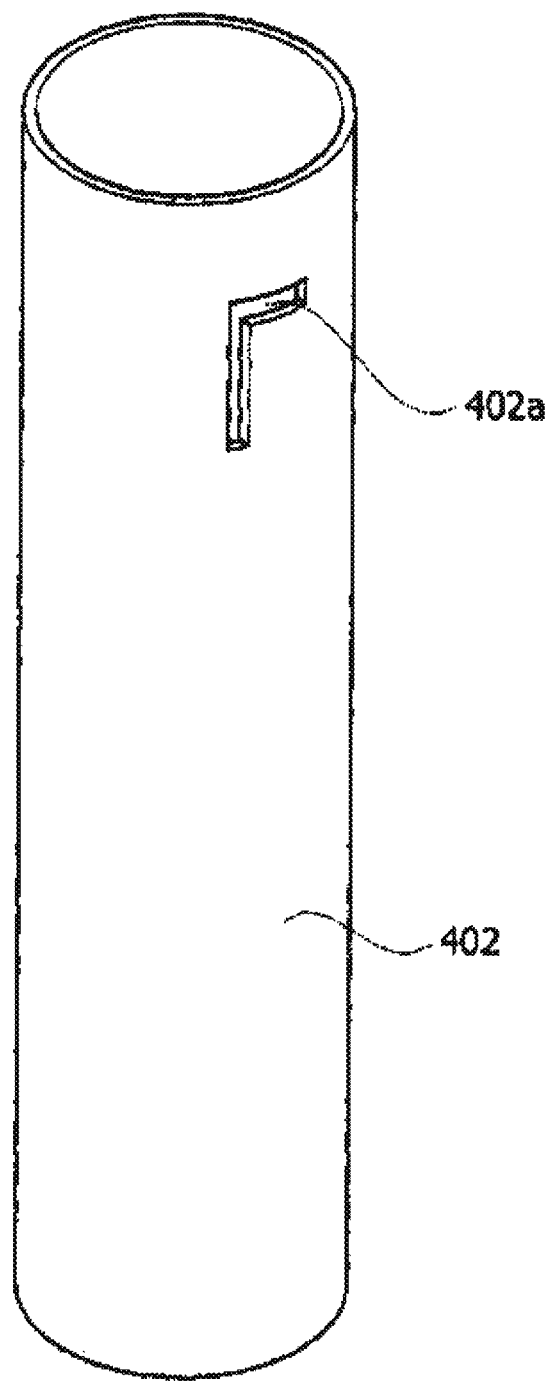
FIG. 12 is a schematic view of a body part of the microlancer of the present invention. 402: body part, 402a: groove
Figure 13:
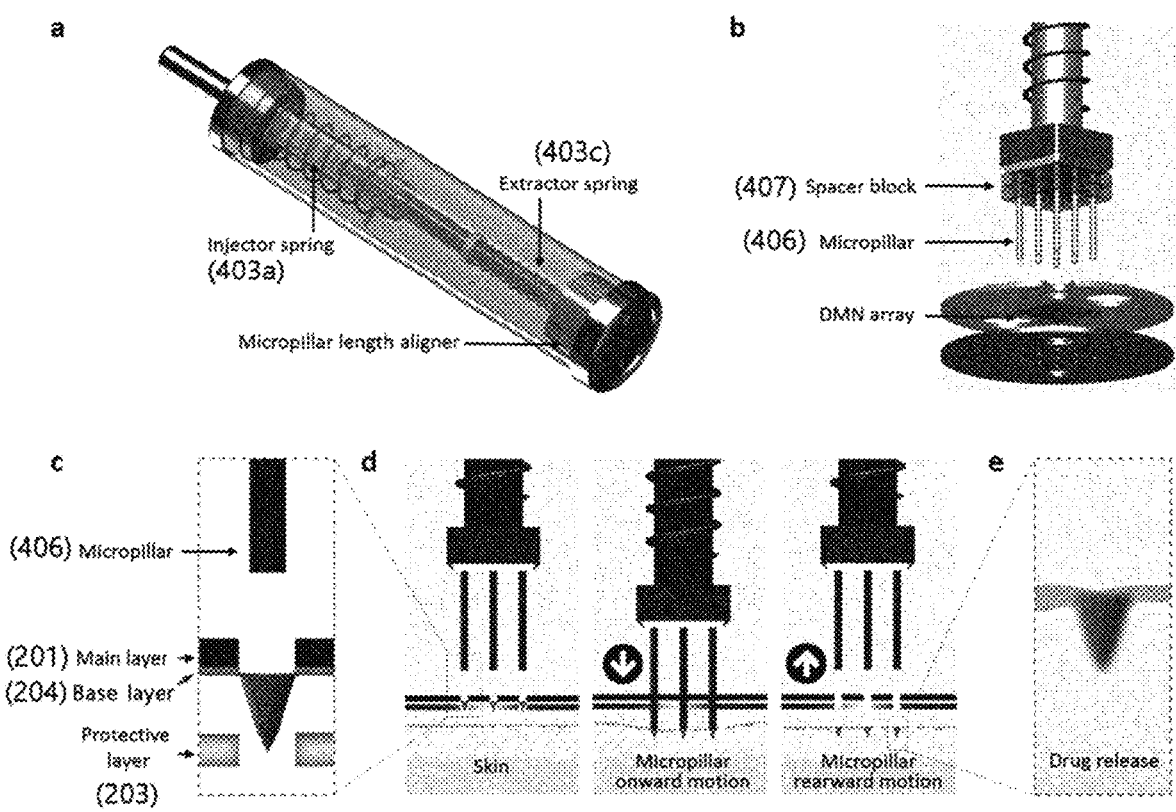
FIG. 13 is a schematic view showing a model of the microlancer of the present invention and an operation method thereof a: Three springs are used to inject or release pillars in the microlancer. An injecting spring applies a force so that the pillars reach the skin present outside a device. On the other hand, one spring (403c) of two extracting springs surrounds the injecting spring, and the other spring (403b) is arranged below the microlancer, and forces the pillars to return into the body part (a housing). A pillar length aligner 408 adjusts a depth of insertion of microneedles (DMNs). b: A 3×3 DMN array included in a top part of the microlancer is shown. By using the microlancer, the pillars move through holes to separate a DMN array from a base layer. Depending on the height and number of spacer blocks, a length of insertion of the pillars may be adjusted, and a depth of insertion of DMNs into the skin may be adjusted. c: For physical separation of DMNs, the positions of the holes and an alignment with the pillars are shown. A bottom part of each of the DMNs has a width slightly larger than the holes. Therefore, the DMNs are weakly brought into contact onto the main layer. A CMC layer provides a base for fabricating the DMNs. Also, a protection layer serves to separate only the DMNs from the main layer other than the surrounding CMC layer. d: The microlancer is used to release the pillars and insert the DMNs into the skin using an injecting spring. Thereafter, the pillars automatically return to the microlancer by two extracting springs. Since the DMNs are not attached to the pillars, the entire insertion and removal processes are performed within one second, and the DMNs are rapidly dissolved into the skin. e: The DMNs are completely and rapidly dissolved into the skin.

The test results obtained by the method are as follows:

A microlancer 40 was designed in a 3×3 array of 5-mm-thick round pillars 406 (r=250 μm) to insert dissolving microneedles (DMNs) into the epidermis and dermis of the skin (see FIGS. 10 and 13). A force generated by a pressure of a patient's thumb is provided along the axis of the microlancer of the present invention. At the same time, an injecting spring 403a pushed pillar arrays 202 and 204 at a predetermine load of 206.5 N/m to maintain an exact alignment with respect to the skin. When the patient removed his/her thumb pressure after an injection process, two extracting springs 403b and 403c forced the pillars to return to a body part 402 of the microlancer. A DMN insertion depth was adjusted by a pillar length alignment system, and determined by an attending physician, depending on the respective patients' skin conditions. The DMN insertion depth may, for example, be set as 50 μm, 100 μm, 300 μm, 500 μm, 1 mm, 2 mm, or 2.5 mm; an actual insertion depth is adjusted by the height of a spacer block 407 inserted into the body part (a housing). Therefore, the insertion depth of the DMNs was adjusted by adjusting the height of the spacer block in the microlancer of the present invention (see FIGS. 10 and 13).

Even when any method of fabricating DMNs was applied to form a microlancer, the present inventors manufactured DMNs having a height of 600 μm and a tip radius of 10 μm to have a 3×3 array including round holes (r=252 μm) in order to enable easy and continuous physical separation of the DMNs using the latest method such as droplet-born air blowing (DAB) (27). The hole array was coated with a thin layer of carboxymethyl cellulose (CMC) to prepare a base for fabricating the DMNs. To fabricate the DMNs on the hole array, each hole region was designed with a size of $2\times10^{-3}$ cm$^2$. In this case, these regions had a size of $2.83\times10^{-5}$ cm$^2$ smaller than the bottom width of the most DMNs. Also, since the coating mixture and polymer used for the DMNs were composed of the same substance, a CMC layer was slowly dissolved after fabrication, and became thin, compared to the other region of the coated layer. A protection layer served to insert only the DMNs into the skin, but not the surrounding substance of the base layer (see FIG. 13C). The use of the microlancer by a patient recovered the compressed alignment spring to an equilibrium length. As a result, a force was applied to the pillar through the holes, thereby enabling separation of the DMNs and insertion into the skin. The pillars were immediately compressed to return into the microlancer (see FIG. 13D). Since the insertion of the DMNs was performed through the pillars, the microlancer continuously enabled effective insertion of the DMNs into the skin (see FIG. 13E). The present inventors conducted a mechanical crushing strength test to determine the maximum axial load which could be applied to the DAB-made DMNs. The maximum axial load was approximately 0.498 N, which was a force 8 times higher than the minimum penetration force required to insert the DMNs into the skin (n=9). (25, 31).

Figure 14:
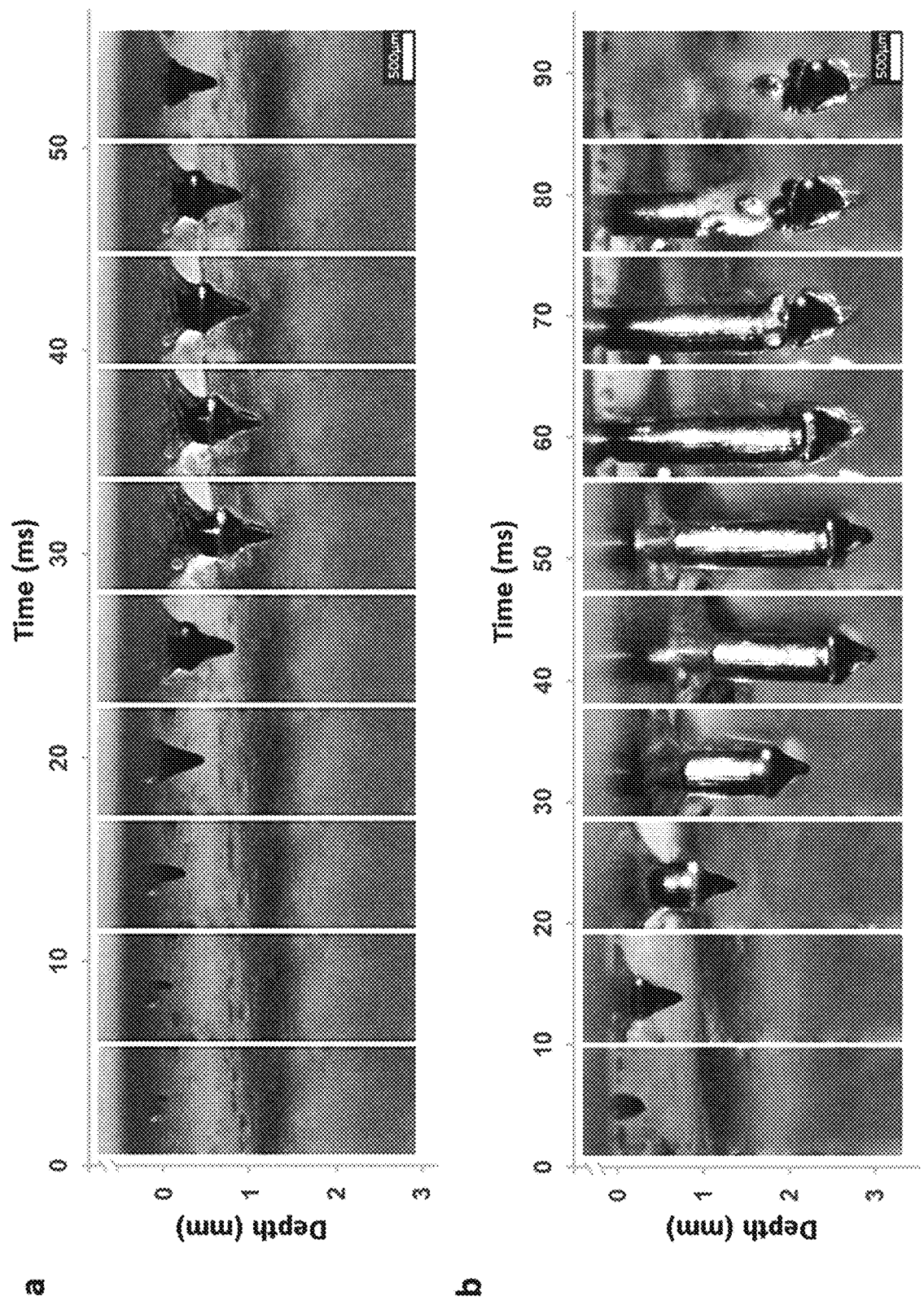
FIG. 14 shows images obtained by photographing a process of inserting DMNs into a 20% polyacrylamide gel using a high-speed video camera. a: The DMNs inserted into the skin to a depth of 50 µm are shown. A complete insertion is performed within 0.5 seconds, and an insertion depth is approximately 650 µm. b: The DMNs are inserted to a depth of 2.5 mm, but not to a depth of 50 µm, and the DMNs are inserted into the gel to a depth of approximately 3 mm. The DMNs are not attached to the pillars, and separated at the moment at which the pillars escape out of the gel.

To visually observe a mechanical operation of the microlancer, the DMNs inserted into a polyacrylamide gel were photographed using a high-speed camera. The polyacrylamide gel is not completely similar to the human skin, but has been widely experimentally used due to penetration and skin-like properties (29,32). Positions of DMN tips were tracked by examining a still picture using microscope calibration software. The insertion depths of a surface part (50 μm) and a bottom part (2.5 mm) were selected as typical adjustable depths by the microlancer. The surface insertion lasted for approximately 0.5 seconds; the DMNs were completely inserted into the gel within 0.3 seconds in this procedure, and the returning of the pillars was completed only within 0.2 seconds after the insertion (see FIG. 14A). Although the DMNs were completely inserted, the holes were formed in the gel by the pillars (pierced). In this drug delivery procedure, a clinical application of the microlancer was very important, and the system of the present invention could be used to deliver the DMNs into the skin without pain. Hereinafter, to test an insertion force of the microlancer, the present inventors prepared a system for inserting the DMNs into a gel to a depth of 2.5 mm. Since the DMNs were inserted deeper into the gel, the DMNs were inserted for an extended insertion time of 0.85 seconds, unlike the insertion to a depth of 50 μm (see FIG. 14B).

Figure 15:
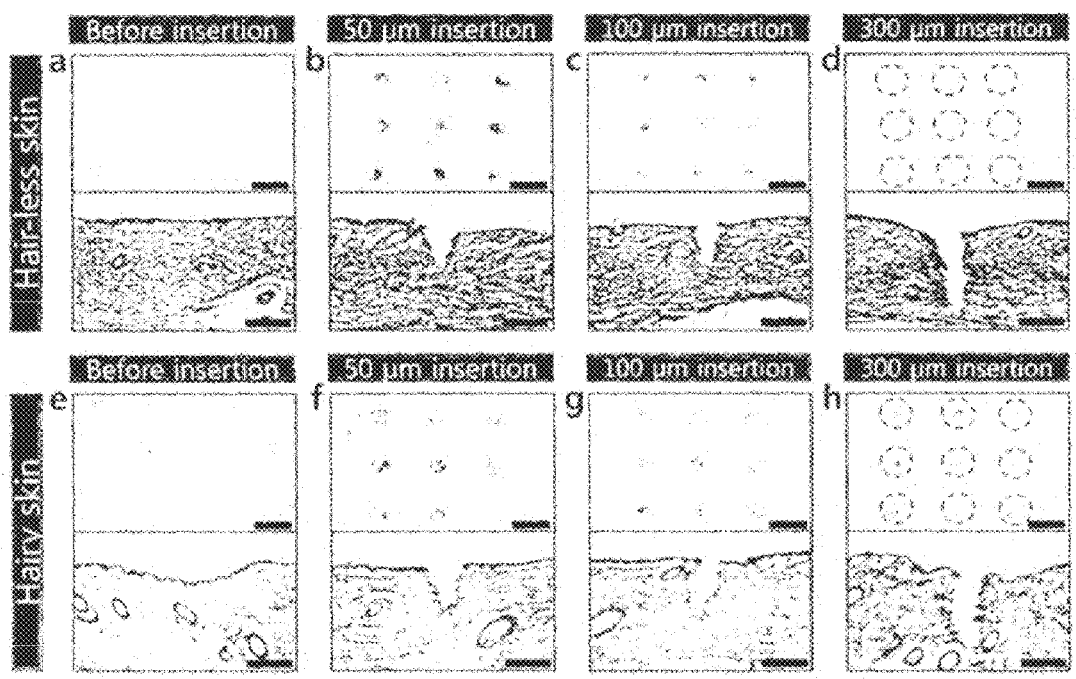
FIG. 15 shows microscopic images and histological test results of hairy or hairless skins from dead pigs and after insertion of the DMNs so as to confirm preciseness and reproducibility of the microlancer. The height of fabricated DMNs is 600 µm. a: Hairless skins from a dead pig before injection of DMNs. b: 600-µm-long DMNs are inserted to a depth of 50 µm. The DMNs are inserted into the skin to a depth of 650 µm. c: Base areas of the DMNs inserted to a depth of 100 µm are observed less clearly, compared to the DMNs inserted to a depth of 50 µm. A histological test shows that the DMNs are inserted into the skin to a depth of 700 µm. d: The DMNs fabricated to be inserted to a depth of 300 µm are inserted into the skin to a depth of 900 µm. A DMN spot array is most faintly observed from the results for three insertion depths. e: The DMNs inserted into the hairy skin to a depth of 50 µm show similar results, compared to when the DMNs are inserted into the hairless skin. f: The DMNs inserted into the skin to a depth of 50 µm were inserted to a similar depth of 650 ±10 µm in average to form insertion spots, compared to when the DMNs were inserted into the hairless skin. g: The DMNs inserted into the hairy skin to a depth of 100 µm are pierced to a depth of 700 µm. h: The DMNs inserted into the hairy skin to a depth of 300 µm show similar results, compared to when the DMNs are inserted into the hairless skin. Scale bar: 2 mm on a microscopic image. Scale bar: 500 µm on a histological image.

All DMN application devices were designed so far to strongly fix a DMN patch in the skin. However, even when a force of 16.4 N/array was applied to the DMNs, the DMNs were not completely inserted into the gel. Therefore, the present inventors designed a microlancer capable of adjusting a depth of insertion of the DMNs into the skin. In this case, the microlancer was used to insert the DMNs to a depth range of 50 μm to 2.5 mm, regardless of the amount of hair present on the skin. To more exactly visualize an insertion area into the skin, hyaluronic acid (HA) DMNs were loaded with a green dye. Also, a histological test was carried out to determine a desired skin insertion depth regarding an actual skin insertion depth. The present inventors chose the insertion depths of 50 μm, 100 μm and 300 μm to evaluate preciseness of the microlancer. For an incision process, the skin was treated with a 10% methylene blue dye solution. A hairless skin from a dead pig was used instead of the human skin (see FIG. 15A). The DMNs (h=600 μm) inserted into the hairless skin to a depth of 50 μm were clearly observed beneath the skin; such DMNs were inserted into a depth of 650±10 μm in average (see FIG. 15B). The DMNs inserted into the skin to a depth of 100 μm were less clearly observed under a microscope. This histological test showed that the DMNs were pierced into the skin to a depth of 700±20 μm (see FIG. 15C). The DMNs inserted to a depth of 300 μm were pierced to a depth of 900±35 μm, and most faintly observed under an optical microscope (see FIG. 15D). To determine reproducibility and preciseness of the microlancer regardless of the type of the skin or the amount of hair on the skin, a similar experiment was carried out using a hairy skin from a dead pig (see FIG. 15E). The DMNs inserted into the skin to a depth of 50 μm were inserted to a similar depth of 650±10 μm in average to form insertion spots, compared to when the DMNs were inserted into the hairless skin (see FIG. 15F). In the histological test on the DMNs inserted into the hairy skin to depths of 100 μm and 300 μm, the similar results were also obtained, compared to the results obtained when the DMNs were inserted into the hairless skin (FIGS. 15C and 15F). These results proved that the microlancer of the present invention could be used to adjust the insertion depth regardless of the type of the skin or the amount of hair on the skin. Accordingly, the microlancer was effectively applicable to various skin types.

Figure 16A:
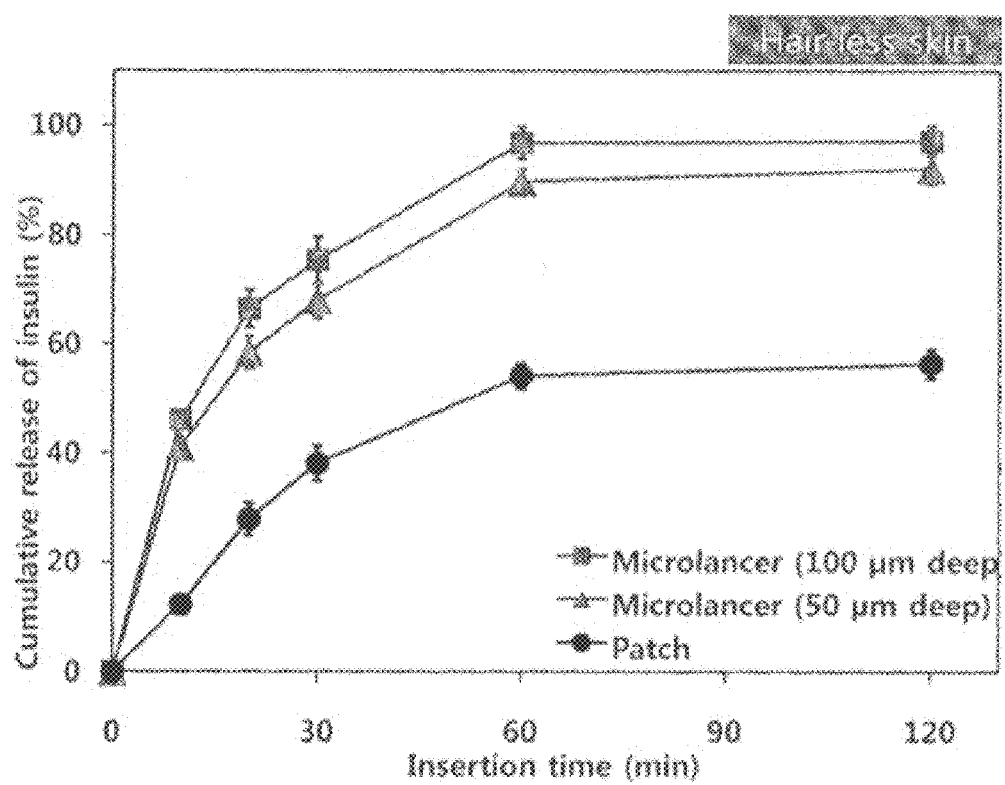
FIGS. 16A to 16C show insulin release profiles obtained in Franz diffusion cells in the case of a DMN patch (black, circle marks) and when a microlancer is inserted to a depth of 50 µm (blue, triangle marks) and 100 µm (red, square marks).
Figure 16B:
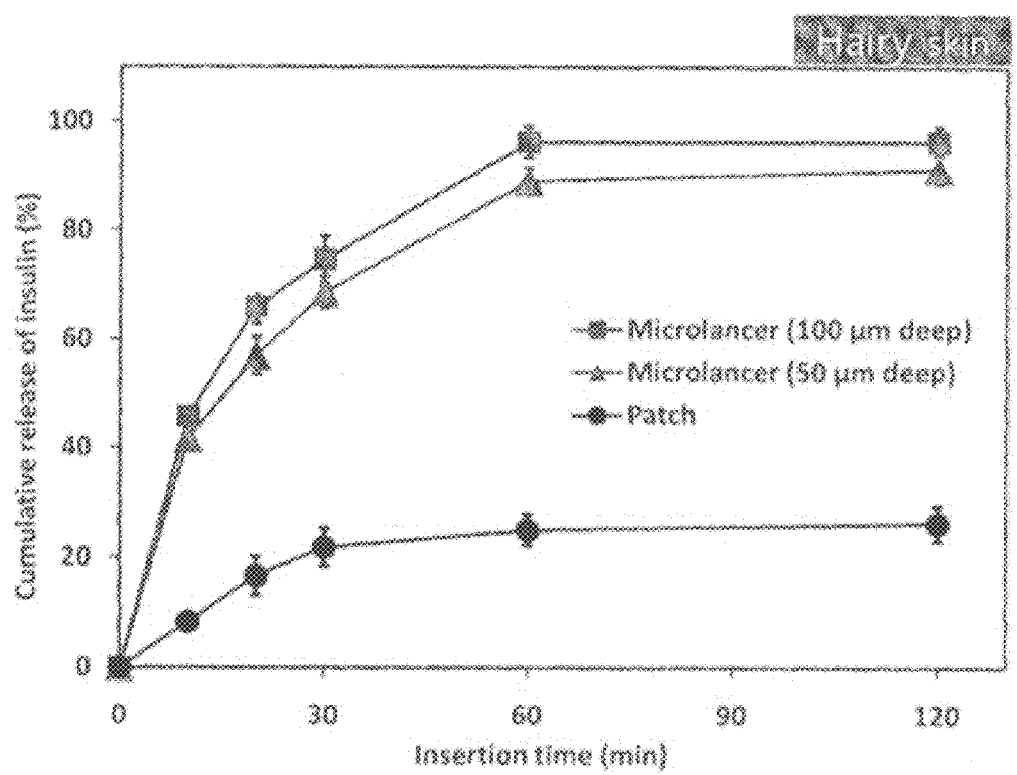

To compare the drug release efficiencies of the DMN patch and the microlancer, Franz diffusion cells for transport by Humalog insulin-loaded DMNs were prepared. Receptor and donor cells having a temperature similar to the human body were used as the Franz diffusion cells, and thus acted similarly on the natural circulation of the blood through the human body. The insulin (0.2 IU)-loaded CMC DMNs were applied onto a 1×1 cm skin region from a dead pig; tests were carried out on two DMN groups of DMN patch and microlancer (n=3 per group). Skin fragments were fixed on Franz diffusion cells, and pressurized with a pinch clamp. Samples were taken from the receptor at points of time of 10 minutes, 20 minutes, 30 minutes, 60 minutes, and 120 minutes, and insulin in each of the samples was quantified using an ELISA kit (n=3 per group). As a result, the insulin release profiles of the microlancer and the DMN patch were very different after 10 minutes. After the elapse of 10 minutes, only 12±2% of the total insulin was released from the DMN patch, but 46±1% (p<0.0001) of the total insulin was already released from the microlancer (a depth of 50 μm). After 2 hours of the application, 56±5% of the total insulin was released from the DMN patch, but 92±2% (p<0.0001) of the total insulin was released from the microlancer (see FIG. 16A). To analyze the efficiency of DMN insertion into the hairy skin, Franz diffusion cells were prepared under the same conditions except the hairy skin. The insulin release profile was determined at the same time intervals as in the first experiment. After the elapse of 2 hours, the insulin release profile of the DMNs inserted by the microlancer was shown to be similar, but only 26±2% of the total insulin was released from the DMNs inserted by the patch (p=0.0001) (see FIG. 16B). These results showed that the microlancer of the present invention could be used to insert the DMNs into the hairy or hairless skin with the same level of efficiency, unlike the DMN patch.

Even when the DMNs were inserted into the epidermal layer of the skins from the dead pig to a depth of 50 μm, approximately 92% of the drug was delivered. The present inventors assumed that the 8% of the remaining drug existed as a surface-residual drug. Therefore, the pillars were prepared to insert the DMN into the hairy or hairless skin to a depth of 100 μm. The drug release profile of the DMNs inserted to a depth of 100 μm reached 97±3%, which increased by approximately 5%, compared to when the DMNs were inserted to a depth of 50 μm (p<0.0001). These results showed that the DMNs inserted to just a depth of 50 μm could not be 100% released; however, the deeper insertion means a higher release rate.

Figure 16C:
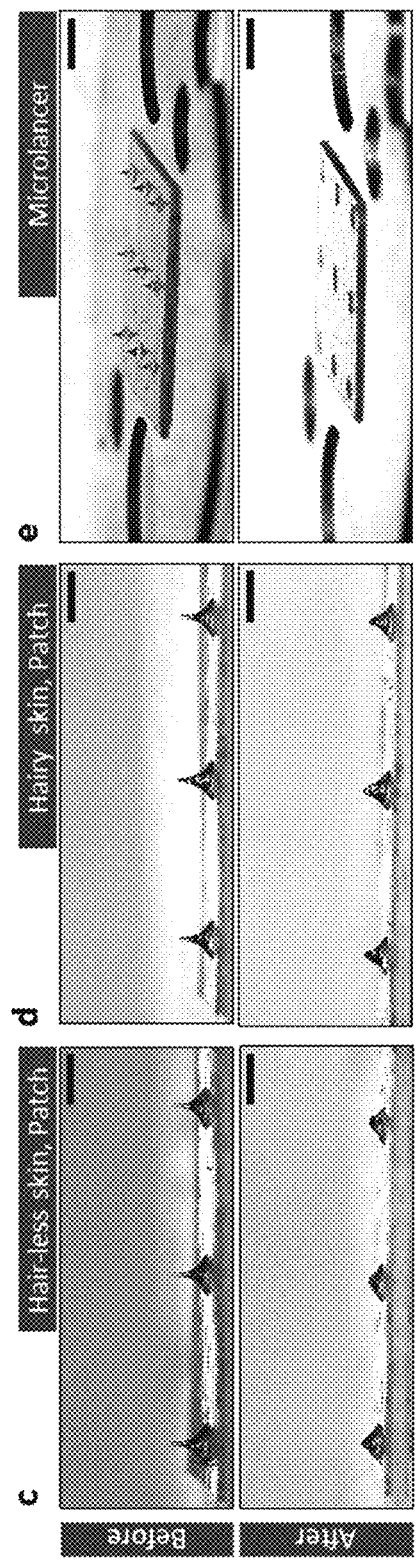

To examine a difference between the drug delivery profiles, the present inventors compared the physical shapes of the DMNs before/after 2 hours of the application using an optical microscope. It was observed that the DMNs arranged on the patch were not completely inserted into the skins from the dead pig. In the hairless skin, approximately ⅓ of the DMNs remained intact on the patch (see 'c' of FIG. 16C). In the hairy skin, only a small amount of the DMNs were dissolved, and approximately 70% of the DMNs remained intact on the patch (see 'd' of FIG. 16C). Unlike the patch, the DMNs arranged on the holes of the microlancer were completely separated from the base, and then successfully inserted into the skin (see 'e' of FIG. 16C). The drug release profiles of the microlancer was observed to be the same as in the hairless and hairy skin, but only approximately 26% to 56% of the total insulin was released from the DMN patch. The results showed that the microlancer could completely insert the insulin-loaded DMNs more effectively or at a significant rate, compared to the DMN patch.

To examine the potency of insulin delivered by the DMNs, the biological activity of 0.2 IU insulin were measured before and after encapsulation on the DMNs using an ultra-performance liquid chromatography (UPLC). As a result, it was revealed that the biological activity of the DMNs-loaded insulin was successfully provided (n=3).

Figure 17A:
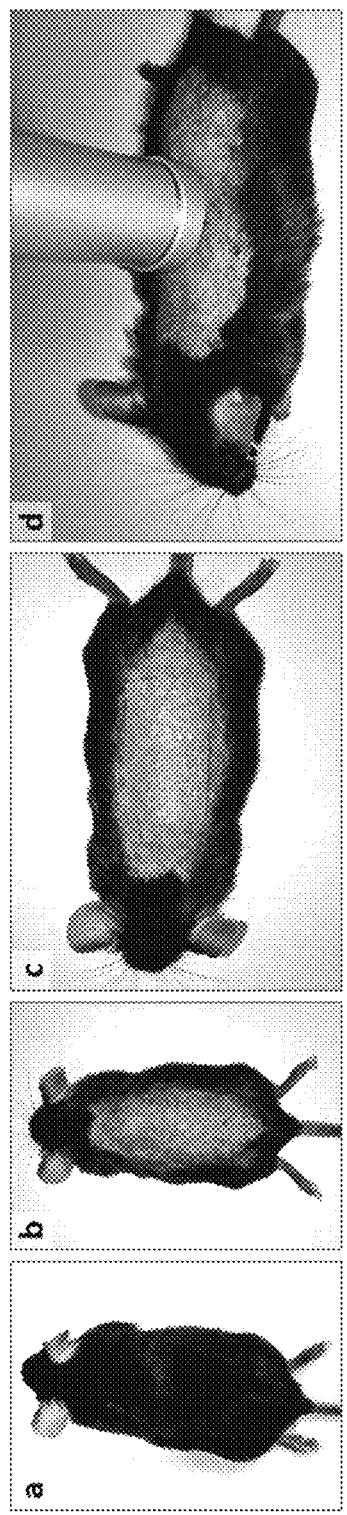
FIGS. 17A to 17C show in vivo images of diabetogenic mice and insulin effects obtained after application of a DMN patch or a microlancer or application using a subcutaneous injection method.
Figure 17B:
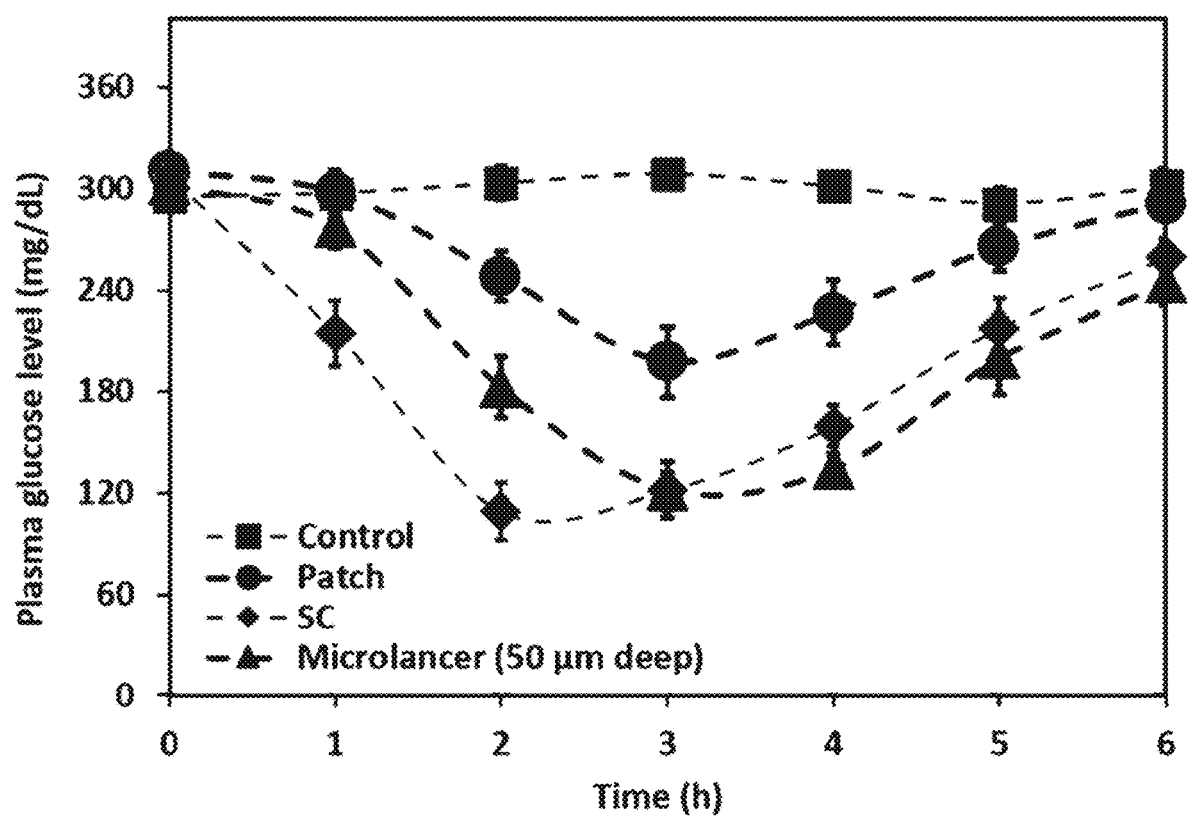

To examine the in vivo delivery efficiency by DMN patch and subcutaneous injection (SC) methods and through the microlancer, insulin was administered to diabetogenic mice using each of the methods, and changes in blood glucose levels were measured. Diabetes was induced in the mice, and a DMN-applied region in the mouse skin was shaved for more exact comparison (see 'a' and 'b' of FIG. 17A). A fabricated DMN array containing 0.2 IU of insulin was applied to the mouse skin using the patch or the microlancer of the present invention (see 'c' and 'd' of FIG. 17A). To compare the DMN delivery efficiency by the subcutaneous injection method to the DMN delivery efficiency through the microlancer, 0.2 IU of insulin was subcutaneously injected to the mice. Meanwhile, the DMNs were inserted into the mouse skin to a depth of 50 μm using the microlancer. A DMN patch was put on the skin of each of the mice, and then fixed with an adhesive tape. Unloaded DMNs were used as the negative control, and inserted to the skins of the control mice using the microlancer. Insulin was administered using each of the methods, and changes in plasma glucose levels in the diabetogenic mice were measured after the elapse of 6 hours (see FIG. 17B). In the case of the DMNs inserted through the microlancer, the plasma glucose level was rapidly dropped from 300 mg/dl to 102 mg/dl; it was also revealed that the insertion through the microlancer was as effective as the subcutaneous injection, and the insulin was directly delivered beneath the dermis. The lowest blood glucose level was observed an hour earlier after the subcutaneous injection, compared to the insertion through the microlancer. It was assumed because the CMC DMN-loaded insulin had a slow diffusion rate. The results of quantification of the plasma glucose levels showed that the lowest plasma glucose level was reduced to 197 mg/dl (p=0.0001), indicating that the DMNs on the patch were less effectively inserted (p=0.0001). The present inventors concluded that the lower plasma glucose level was probably caused by the incomplete insertion of the DMNs by the patch. These results supported the drug release profile results obtained in Franz diffusion cell experiments using the microlancer and the patch (see FIGS. 16A and 16B).

Figure 17C:
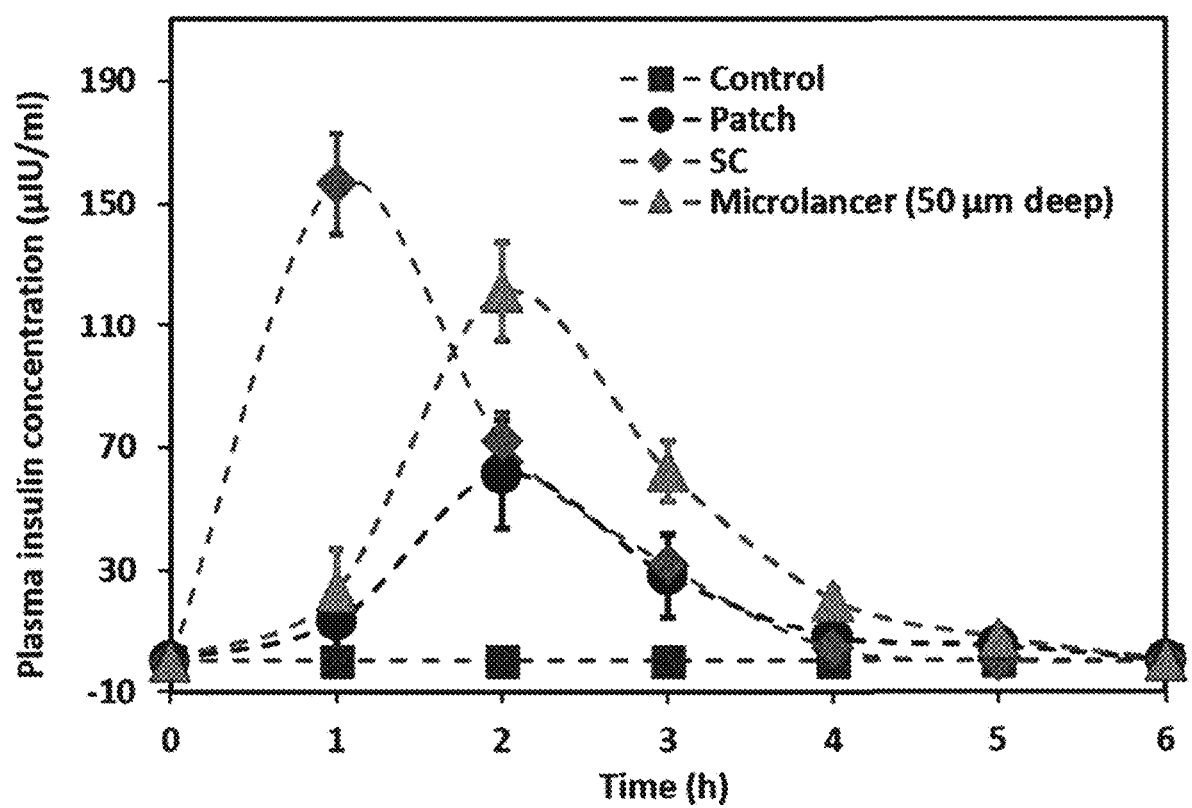
Figure 18:
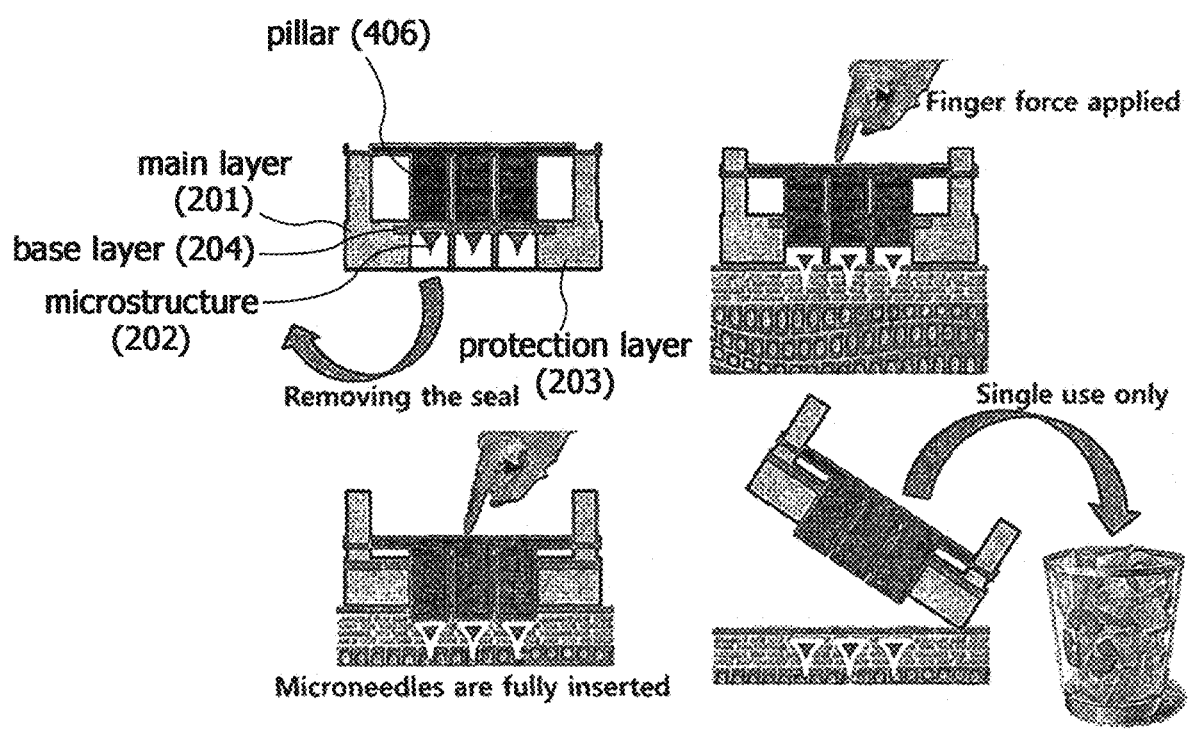
FIG. 18 is a schematic view showing a disposable microlancer of the present invention and a use thereof. The microlancer is operated by a physical force applied from the outside.
Figure 19:
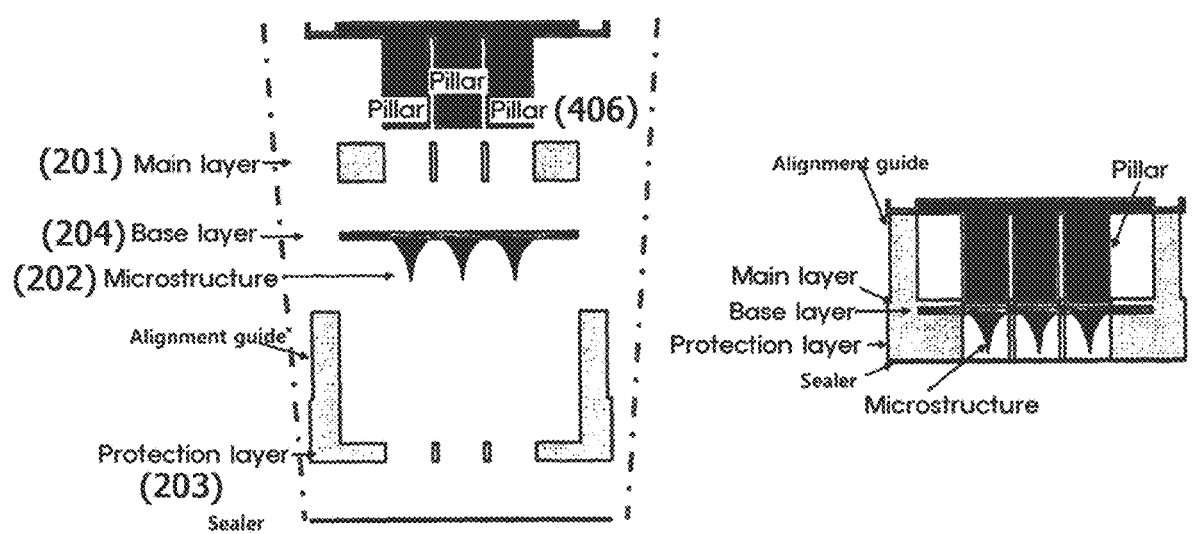
FIG. 19 is a schematic view showing a coupling structure of the disposable microlancer of the present invention.
Figure 2O:
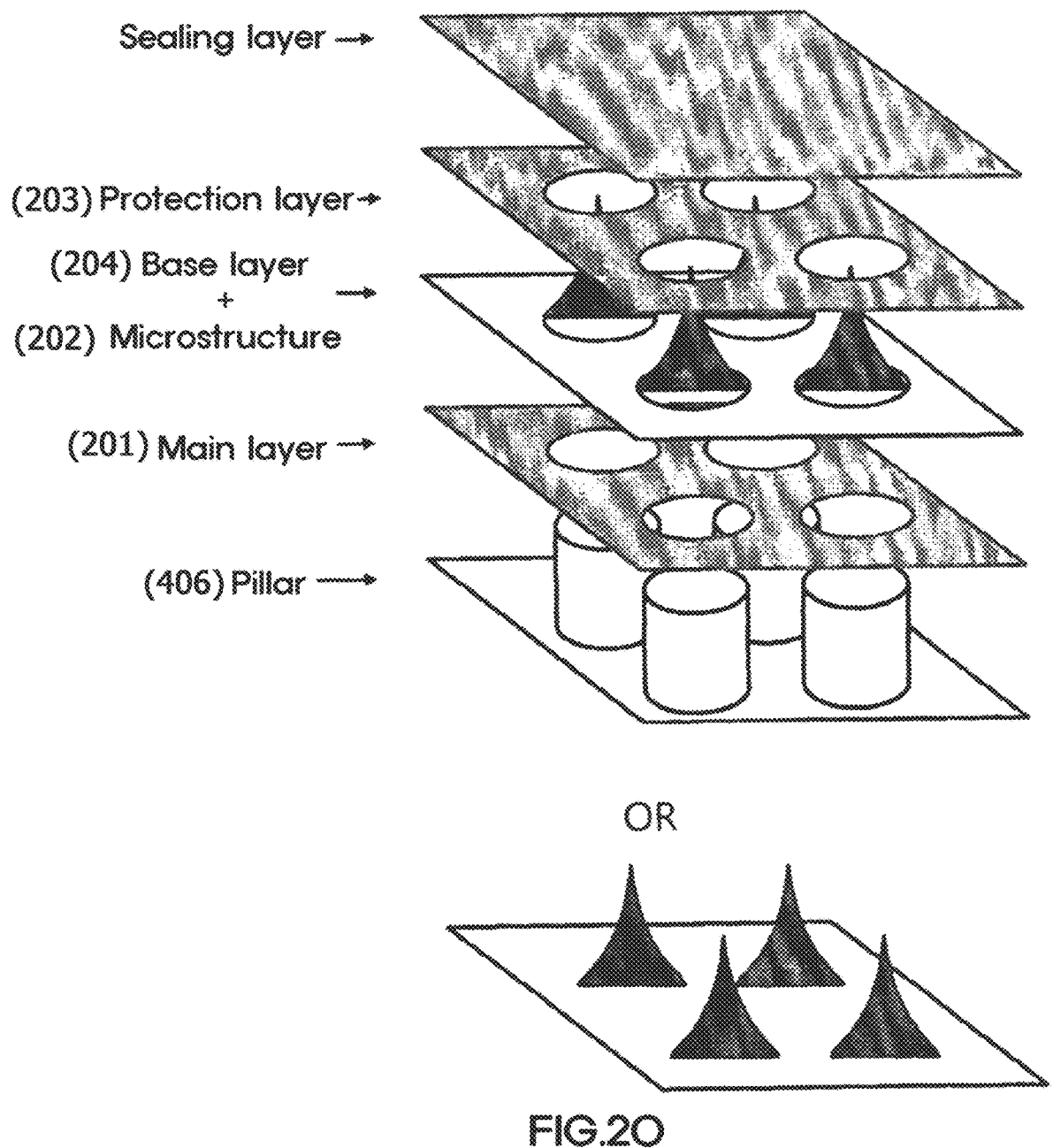
Figure 21:
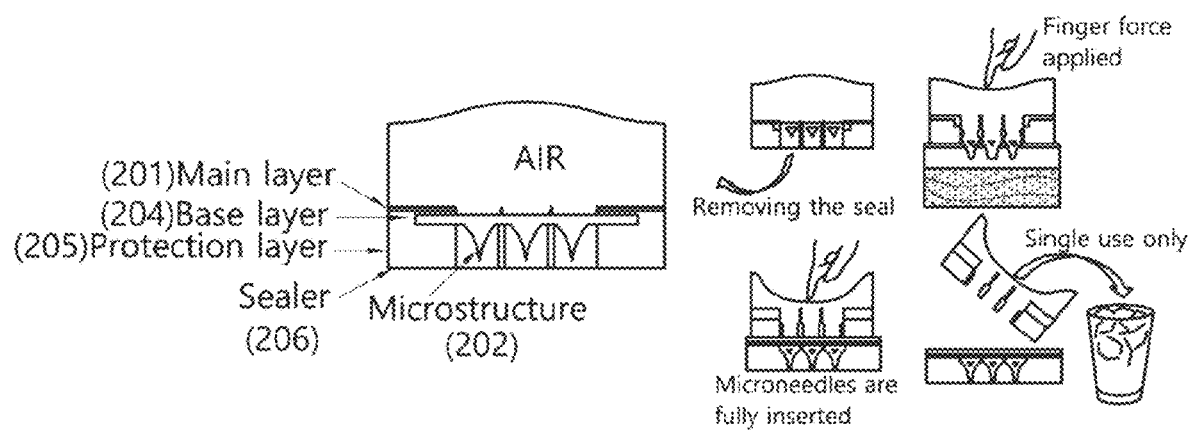
FIG. 21 is a schematic view showing a disposable microlancer of the present invention and a use thereof. Unlike that shown in FIG. 19, the microlancer is operated by an air pressure.
Figure 22:
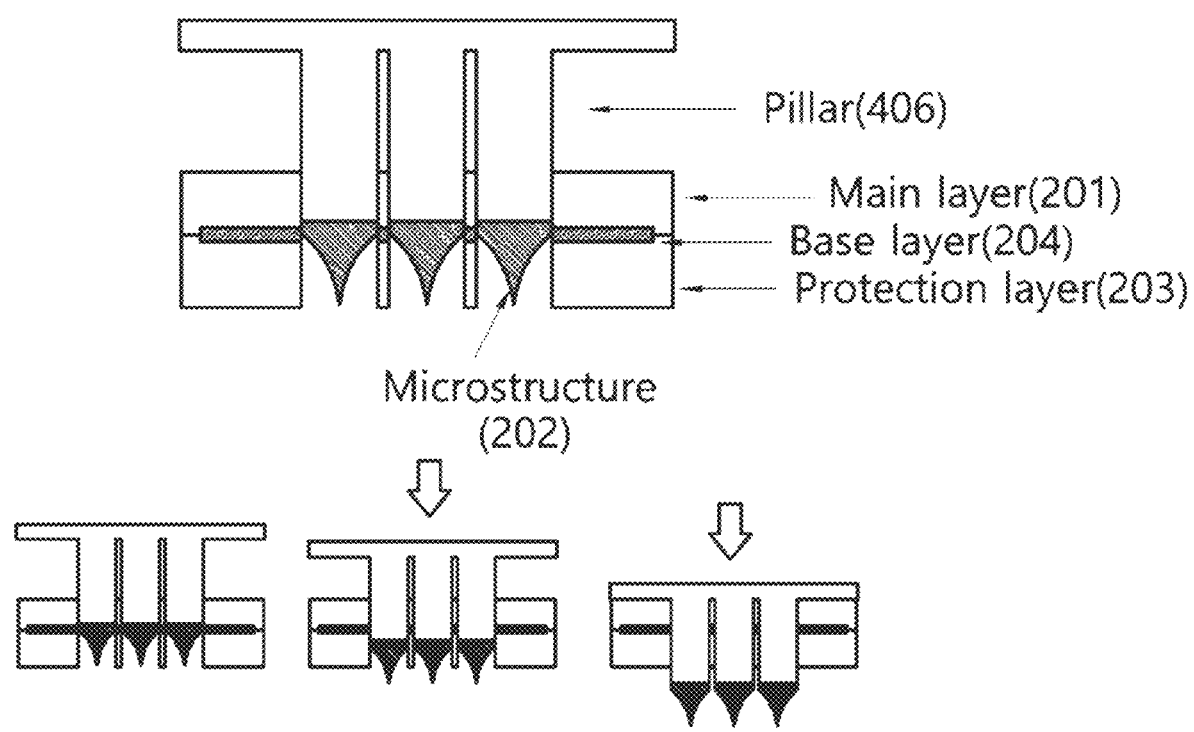
FIG. 22 is a schematic view showing a disposable microlancer of the present invention and a use thereof. Unlike other disposable microlancers, pillars are directly coupled to holes of a main layer without an aligner or a body part.

To test the functions of the DMNs regarding the delivery of insulin into the skin, the plasma insulin concentration in each of the mice was measured for 6 hours of the treatment. Peaks for the plasma insulin concentration in the subcutaneously injected group were observed after an hour, but peaks for the plasma insulin concentration in the DMN patch-treated group and the microlancer-treated group were observed after 2 hours (FIG. 17C). The maximum plasma insulin concentration in the subcutaneously injected group was 156 μIU/ml; however, the maximum plasma insulin concentration in the DMN patch-treated group was shown to be 57 μIU/ml, which accounted for approximately 36% of the total amount of the loaded insulin (p=0.0277). The maximum plasma insulin concentration in the microlancer-treated group was 124 μIU/ml, which accounted for approximately 80% of the total amount of the loaded insulin. The plasma insulin was not detected in the control, and the plasma insulin concentration was maintained at 0 during a test time.

These results showed that the DMNs were effectively applicable without a patch for the first time. The present inventors combined advantages of the DMN patch and needle-less injector to develop a DMN delivery system which was rapidly applicable, self-injectable and capable of precisely and continuously adjusting the insertion depth. In the system of the present invention, the DMNs were able to be delivered in a more dose-effective manner, thereby minimizing the invasion of the skin. In the conventional technology, most of the DMN application devices had a drawback in that a high pressure force needed to be continuously applied to the patch on the skin, and thus patients felt uncomfortable due to side effects such as infections and/or redness in application sites. However, the microlancer of the present invention used the pillars to insert the DMNs into the skin. As a result, a contact area with the skin was minimized unlike the conventional devices.

To prove the reproducibility and preciseness of the insertion by the microlancer, experiments were performed at varying insertion depths. When the results obtained by the above-described DMN patch and other manufacturing techniques were compared to those obtained through the microlancer, the microlancer had a probability of being more rapid and effective in the delivery of DMN-based drugs. It was more important that patients could adjust a desired dose of a drug to take medicine according to their prescriptions, thereby improving the quality of diabetic patients' lives. Therefore, the microlancer could be used to insert any type of drugs, protein vaccines or biomolecules encapsulated in the DMNs for the purpose of wide clinical applications. Owing to the improved DMN delivery efficiency and minimum invasion effects of the microlancer, the system of the present invention was expected to have a great influence on the vaccine and drug delivery in the future. In recent years, the present inventors have conducted research on treatment for alopecia using the DMNs in order to provide the optimal efficiency and convenience.

REFERENCES

1. Sullivan, S. P., N. Murthy, and M. R. Prausnitz, Minimally invasive protein delivery with rapidly dissolving polymer microneedles. Adv Mater 20, 933-938 (2008).

2. Prausnitz, M. R., S. Mitragotri, and R. Langer, Current status and future potential of transdermal drug delivery. Nat Rev Drug Discov 3, 115-24 (2004).
3. Prausnitz, M. R. and R. Langer, Transdermal drug delivery. Nat Biotechnol 26, 1261-8 (2008).
4. Pond, S. M. and T. N. Tozer, First-pass elimination. Basic concepts and clinical consequences. Clin Pharmacokinet 9, 1-25 (1984).
5. Park, J. H., M. G. Allen, and M. R. Prausnitz, Biodegradable polymer microneedles: fabrication, mechanics and transdermal drug delivery. J Control Release 104, 51-66 (2005).
6. Trim, J. C. and T. S. Elliott, A review of sharps injuries and preventative strategies. J Hosp Infect 53, 237-42 (2003).
7. Nir, Y., et al., Fear of injections in young adults: prevalence and associations. Am J Trop Med Hyg 68, 341-4 (2003).
8. Simonsen, L., et al., Unsafe injections in the developing world and transmission of bloodborne pathogens: a review. Bull World Health Organ 77, 789-800 (1999).
9. Prausnitz, M. R., Microneedles for transdermal drug delivery. Adv Drug Deliv Rev 56, 581-7 (2004).
10. Tuan-Mahmood, T. M., et al., Microneedles for intradermal and transdermal drug delivery. Eur J Pharm Sci (2013).
11. Lee, K. and H. Jung, Drawing lithography for microneedles: a review of fundamentals and biomedical applications. Biomaterials 33, 7309-26 (2012).
12. McAllister, D. V., et al., Microfabricated needles for transdermal delivery of macromolecules and nanoparticles: fabrication methods and transport studies. Proc Natl Acad Sci USA 100, 13755-60 (2003).
13. Kaushik, S., et al., Lack of pain associated with microfabricated microneedles. Anesth Analg 92, 502-4 (2001).
14. Miksza, J. A., et al., Improved genetic immunization via micromechanical disruption of skin-barrier function and targeted epidermal delivery. Nat Med 8, 415-9 (2002).
15. Liu, S., et al., The development and characteristics of novel microneedle arrays fabricated from hyaluronic acid, and their application in the transdermal delivery of insulin. J Control Release 161, 933-41 (2012).
16. Lee, K., et al., Drawing lithography: three-dimensional fabrication of an ultrahigh-aspect-ratio microneedle. Adv Mater 22, 483-6 (2010).
17. Lee, J. W., et al., Dissolving microneedle patch for transdermal delivery of human growth hormone. Small 7, 531-9 (2011).
18. Lee, K., C. Y. Lee, and H. Jung, Dissolving microneedles for transdermal drug administration prepared by stepwise controlled drawing of maltose. Biomaterials 32, 3134-40 (2011).
19. Lee, J. W., J. H. Park, and M. R. Prausnitz, Dissolving microneedles for transdermal drug delivery. Biomaterials 29, 2113-24 (2008).
20. Chu, L. Y. and M. R. Prausnitz, Separable arrowhead microneedles. J Control Release 149, 242-9 (2011).
21. Chen, X., et al., Improving the reach of vaccines to low-resource regions, with a needle-free vaccine delivery device and long-term thermostabilization. J Control Release 152, 349-55 (2011).
22. Van Damme, P., et al., Safety and efficacy of a novel microneedle device for dose sparing intradermal influenza vaccination in healthy adults. Vaccine 27, 454-9 (2009).
23. van der Maaden, K., W. Jiskoot, and J. Bouwstra, Microneedle technologies for (trans)dermal drug and vaccine delivery. J Control Release 161, 645-55 (2012).
24. Chen, M. C., et al., Fully embeddable chitosan microneedles as a sustained release depot for intradermal vaccination. Biomaterials 34, 3077-86 (2013).
25. Sullivan, S. P., et al., Dissolving polymer microneedle patches for influenza vaccination. Nat Med 16, 915-20 (2010).
26. Trookman, N. S., R. L. Rizer, and T. Weber, Irritation and allergy patch test analysis of topical treatments commonly used in wound care: evaluation on normal and compromised skin. J Am Acad Dermatol 64, 16-22 (2011).
27. Kim, J. D., et al., Droplet-born air blowing: Novel dissolving microneedle fabrication. J Control Release 170, 430-6 (2013).
28. Moga, K. A., et al., Rapidly-dissolvable microneedle patches via a highly scalable and reproducible soft lithography approach. Adv Mater 25, 5060-6 (2013).
29. Taberner, A., N. C. Hogan, and I. W. Hunter, Needle-free jet injection using real-time controlled linear Lorentz-force actuators. Med Eng Phys 34, 1228-35 (2012).
30. Engwerda, E. E., C. J. Tack, and B. E. de Galan, *Needle free jet injection of rapid-acting insulin improves early postprandial glucose control in patients with diabetes.* Diabetes Care 36, 3436-41 (2013).
31. Davis, S. P., et al., *Insertion of microneedles into skin: measurement and prediction of insertion force and needle fracture force.* J Biomech 37, 1155-63 (2004).
32. Stachowiak, J. C., et al., *Dynamic control of needle free jet injection.* J Control Release 135, 104-12 (2009).
33. Donnelly, R. F., et al., *Optical coherence tomography is a valuable tool in the study of the effects of microneedle geometry on skin penetration characteristics and in-skin dissolution.* J Control Release 147, 333-41 (2010).

BRIEF DESCRIPTION OF PARTS

10: shooting microstructure I, 101: main layer, 101a: holes of main layer, 101b: surface of main layer, 102: microstructures (microneedles), 103: protection layer, 103a: holes of protection layer.

20: shooting microstructure II, 201: main layer, 201a: holes of main layer, 202: microstructures (microneedles), 203: protection layer, 203a: holes of protection layer, 204: base layer, 204a: holes of base layer.

30: shooting device, 301: body part, 302: top part, 302a: holes of top part, 303: connection part.

40: shooting device (shooting microlancer), 401: top part, 402: body part, 402a: groove, 403a: inner injecting spring, 403b: extracting spring, 403c: outer extracting spring, 404: button, 405: pin, 406: movable pillar, 407: spacer, 408: aligner, 409: auxiliary pipe, 409a: slope, 410: connection pipe, 410a: pin hole, 411: connection pipe.

The present invention has been described in detail. However, it should be understood that the detailed description and specific examples, while indicating embodiments of the invention, are given by way of illustration only, since various changes and modifications within the spirit and scope of the invention will become apparent to those skilled in the art from this detailed description.

The invention claimed is:

1. A device comprising:
   a main layer having a plurality of holes formed therethrough; and
   a base layer placed on the main layer in contact with the main layer; and
   microstructures placed over the base layer such that each microstructure is aligned with one of the plurality of holes of the main layer, wherein the base layer is a unitary layer comprising microstructure regions over which the microstructures are placed and no-microstructure regions over which no microstructures are placed, and wherein the microstructure regions of the base layer are configured to be separated from the no-microstructure regions of the base layer when sufficient pressure is applied to the microstructure regions in a direction from the main layer toward the base layer such that the microstructure regions separated from the no-microstructure regions are injected together with the microstructures into the skin in the direction from the main layer toward the base layer to leave holes in the base layer while maintaining no-microstructure regions on the base layer.

2. The device of claim 1, further comprising a protection layer placed over the base layer such that the base layer is disposed between the protection layer and the main layer, the protection layer comprising a plurality of holes, each of the plurality of holes of the protection layer configured to receive one of the microstructures.

3. The device of claim 1, wherein the microstructure regions of the base layer have a strength weaker than that of the no-microstructure regions of the base layer.

4. The device of claim 1, further comprising movable pillars,
wherein each of the movable pillars is configured to move through one of the plurality of holes of the main layer to push the base layer and one of the microstructures placed over the base layer.

5. The device of claim 1 further comprising:
a body configured to apply pressure to the microstructure regions of the base layer through the plurality of holes of the main layer.

6. The device of claim 5, wherein the body comprises a plurality of pushing pressure transmission channels connected to the plurality of holes of the main layer.

7. The device of claim 5, wherein the device further comprises a pushing pressure generation unit configured to generate pressure applied to the microstructure regions of the base layer.

8. The device of claim 1, wherein the device further comprises a body and movable pillars arranged in the body, wherein the movable pillars are configured to move through the plurality of holes of the main layer beyond a top surface of the device, and further configured to push the microstructures during movement of the movable pillars.

9. The device of claim 8, wherein each of the movable pillars comprises a hollow structure including at least one pillar hole, and the pressure is applied to one of the microstructure regions of the base layer through the at least one pillar hole.

10. The device of claim 8, wherein the device further comprises a spacer mountable in the body and configured to adjust a discharge height of the movable pillars.

11. The device of claim 8, wherein the device further comprises an aligner configured to provide a moving path for each of the movable pillars.

* * * * *